United States Patent
Mirov et al.

(10) Patent No.: US 10,194,809 B2
(45) Date of Patent: Feb. 5, 2019

(54) INTEGRATED ELECTRONICS FOR PHOTOPLETHYSMOGRAPHY AND ELECTROCARDIOGRAPHY

(71) Applicant: Verily Life Sciences LLC, Mountain View, CA (US)

(72) Inventors: Russell Norman Mirov, Los Altos, CA (US); John Navil Joseph, San Jose, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 593 days.

(21) Appl. No.: 14/833,195

(22) Filed: Aug. 24, 2015

(65) Prior Publication Data

US 2017/0055845 A1   Mar. 2, 2017

(51) Int. Cl.
| | |
|---|---|
| *A61B 5/04* | (2006.01) |
| *A61B 5/0205* | (2006.01) |
| *A61B 5/00* | (2006.01) |
| *A61B 5/024* | (2006.01) |
| *A61B 5/0404* | (2006.01) |
| *A61B 5/0402* | (2006.01) |
| *A61B 5/1455* | (2006.01) |

(Continued)

(52) U.S. Cl.
CPC .......... *A61B 5/0205* (2013.01); *A61B 5/0006* (2013.01); *A61B 5/02427* (2013.01); *A61B 5/0404* (2013.01); *A61B 5/04012* (2013.01); *A61B 5/6824* (2013.01); *A61B 5/7225* (2013.01); *A61B 5/742* (2013.01);

(Continued)

(58) Field of Classification Search
USPC ................................................ 600/509, 513
See application file for complete search history.

(56) References Cited

U.S. PATENT DOCUMENTS

| | | |
|---|---|---|
| 5,738,104 A | 4/1998 | Lo et al. |
| 5,876,350 A | 3/1999 | Lo et al. |

(Continued)

FOREIGN PATENT DOCUMENTS

| | | |
|---|---|---|
| EP | 0861045 B1 | 8/2002 |
| WO | 2015017563 A1 | 2/2015 |

OTHER PUBLICATIONS

Analog Devices, Inc., Data Sheet for AD8232, "Single-Lead, Heart Rate Monitor Front End," 2012, 28 pages.

(Continued)

*Primary Examiner* — Nicole F Johnson
(74) *Attorney, Agent, or Firm* — McDonnell Boehnen Hulbert & Berghoff LLP

(57) ABSTRACT

Devices and systems are provided to electrically and optically detect hemodynamic properties of a body. Such devices are configured to detect electrocardiographic signals and photoplethysmographic signals and to operate a single analog-to-digital converter (ADC) to sample one or more of each of such signals. This includes operating a multiplexer to connect electrical signals related to the detected optical and electrical properties to the single ADC during respective different sampling times or periods. This can include connecting the detected electrocardiographic signals and photoplethysmographic signals to the ADC during alternating periods of time. Using a single ADC to sample one or more of each of electrocardiographic signals and photoplethysmographic signals can provide samples of such signals that have a relative timing that is known, stable, and controllable.

20 Claims, 8 Drawing Sheets

(51) Int. Cl.
　　　*A61B 5/021*　　　(2006.01)
　　　*A61B 5/026*　　　(2006.01)

(52) U.S. Cl.
　　　CPC ............ *A61B 5/0002* (2013.01); *A61B 5/021* (2013.01); *A61B 5/0261* (2013.01); *A61B 5/02125* (2013.01); *A61B 5/0402* (2013.01); *A61B 5/14551* (2013.01); *A61B 5/14552* (2013.01)

(56) References Cited

U.S. PATENT DOCUMENTS

| | | |
|---|---|---|
| 8,369,936 B2 | 2/2013 | Farringdon et al. |
| 2005/0249037 A1 | 11/2005 | Kohn et al. |
| 2007/0299330 A1* | 12/2007 | Couronne .......... A61B 5/02416 600/368 |
| 2008/0183232 A1 | 7/2008 | Voss et al. |
| 2013/0137938 A1 | 5/2013 | Peters et al. |

OTHER PUBLICATIONS

Broeders, Jan-Hein, "Predicting and Finding your Limits!," Technical Article MS-2385, Analog Devices, Inc., 2012, 3 pages.
Oregon Scientific, Heart Rate Monitor Walch with Calorie Counter, Model: IHM80004, User Manual, 2010, 2 pages.
Oregon Scientific, Touch Strapless Heart Rate Monitor, Model: SE338/SE338M, User Manual, 2011, 2 pages.
Sportline, Inc., Solo 910 Heart Rate Walch, 2006, 18 pages.
International Search Report and Written Opinion of International Application No. PCT/US2016/039678 dated Oct. 31, 2016.

\* cited by examiner

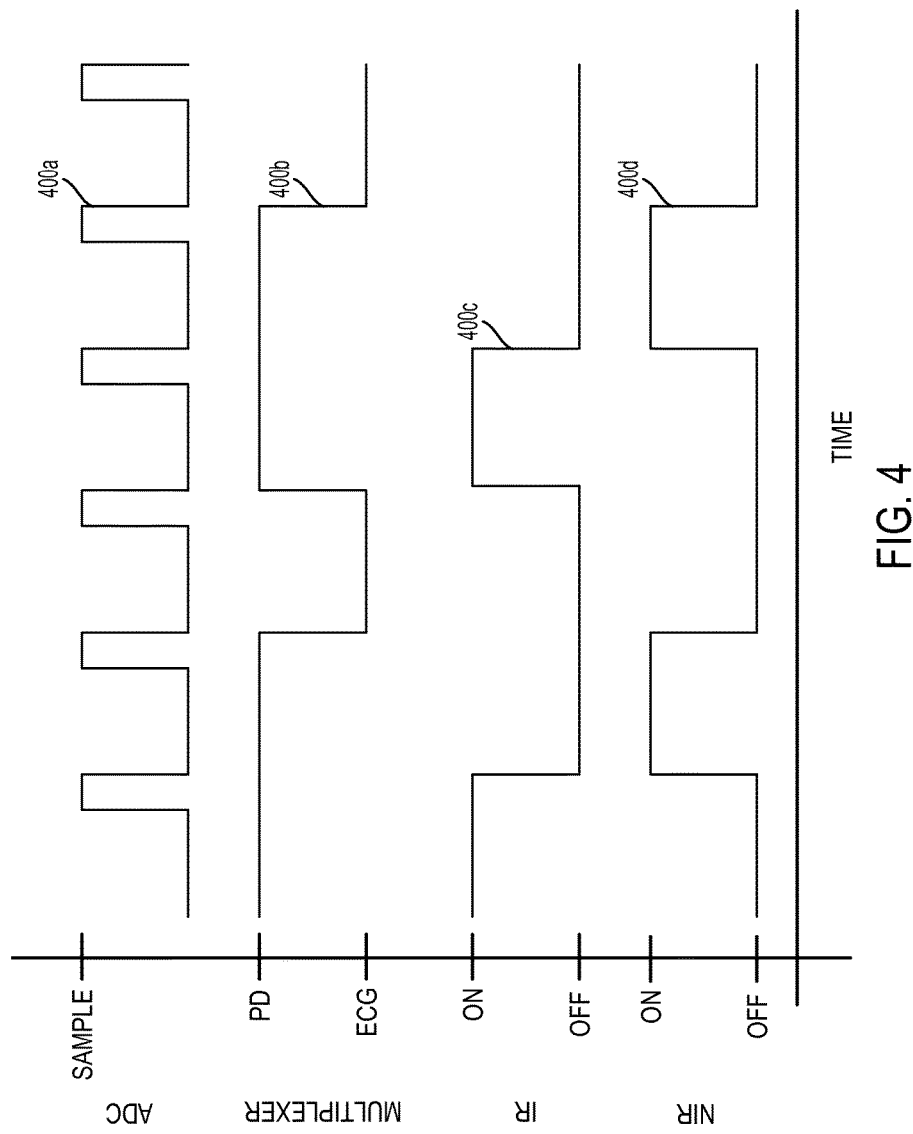

though the methods, systems, and devices may be used

INTEGRATED ELECTRONICS FOR PHOTOPLETHYSMOGRAPHY AND ELECTROCARDIOGRAPHY

BACKGROUND

Unless otherwise indicated herein, the materials described in this section are not prior art to the claims in this application and are not admitted to be prior art by inclusion in this section.

A variety of applications can be provided by wearable devices, e.g., devices configured to be mounted to a wrist or other location of a user's body. Such devices can provide information and/or communications functions to the user (e.g., by providing an indication of the current time or the user's location, by providing the content of an email received by the user). Such devices could include one or more sensors configured to detect properties of the user's body (e.g., a blood pressure, a heart rate, a blood oxygen saturation, electrical activity of the heart) and/or of the environment of the user (e.g., an ambient temperature, a barometric pressure) and to record, provide indications of, communicate to external systems, or otherwise use such detected properties. In some examples, such a wearable device can be configured to connect to an external system, e.g., to receive energy from the external system to recharge a battery of the wearable device, to communicate with/via the external system, or to provide some other application of the wearable device.

SUMMARY

Some embodiments of the present disclosure provide a system including: (i) a light emitter that is configured to illuminate a portion of subsurface vasculature via an external body surface; (ii) a photodetector that is configured to receive light emitted from the portion of subsurface vasculature responsive to illumination by the light emitter; (iii) an electrocardiogram sensor that is configured to detect an electrocardiographic signal via the external body surface; (iv) an amplifier; (v) a multiplexer that is electrically connected to an output of the photodetector, an output of the electrocardiogram sensor, and an input of the amplifier and that is controllable to selectively connect the output of the photodetector and the output of the electrocardiogram sensor to the input of the amplifier; (vi) an analog-to-digital converter that is configured to generate digital codes based on an output of the amplifier; and (vii) a controller. The controller is configured to perform controller operations including: (a) operating the light emitter, during a first plurality of specified periods of time, to illuminate the portion of subsurface vasculature; (b) operating the multiplexer, during the first plurality of specified periods of time, to connect the output of the photodetector to the input of the amplifier; (c) operating the analog-to-digital converter to generate a first plurality of digital codes based on the output of the amplifier during the first plurality of specified periods of time; (d) operating the multiplexer, during a second plurality of specified periods of time, to connect the output of the electrocardiogram sensor to the input of the amplifier; and (e) operating the analog-to-digital converter to generate a second plurality of digital codes based on the output of the amplifier during the second plurality of specified periods of time.

Some embodiments of the present disclosure provide a method including: (i) illuminating, by a light emitter operated by a controller during a first plurality of specified periods of time, a portion of subsurface vasculature via an external body surface; (ii) connecting, by a multiplexer operated by the controller during the first plurality of specified periods of time, an output of a photodetector to an input of an amplifier, wherein the photodetector is configured to receive light emitted from the portion of subsurface vasculature responsive to illumination by the light emitter; (iii) generating, by an analog-to-digital converter operated by the controller during the first plurality of specified periods of time, a first plurality of digital codes based on the output of the amplifier; (iv) connecting, by the multiplexer operated by the controller during a second plurality of specified periods of time, an output of an electrocardiogram sensor to the input of the amplifier, wherein the electrocardiogram sensor is configured to detect an electrocardiographic signal via the external body surface; and (v) generating, by the analog-to-digital converter operated by the controller during the second plurality of specified periods of time, a second plurality of digital codes based on the output of the amplifier.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4 illustrates the timing of operation of elements of a system configured to detect optical and electrocardiographic signals.

DETAILED DESCRIPTION

Figure 1:
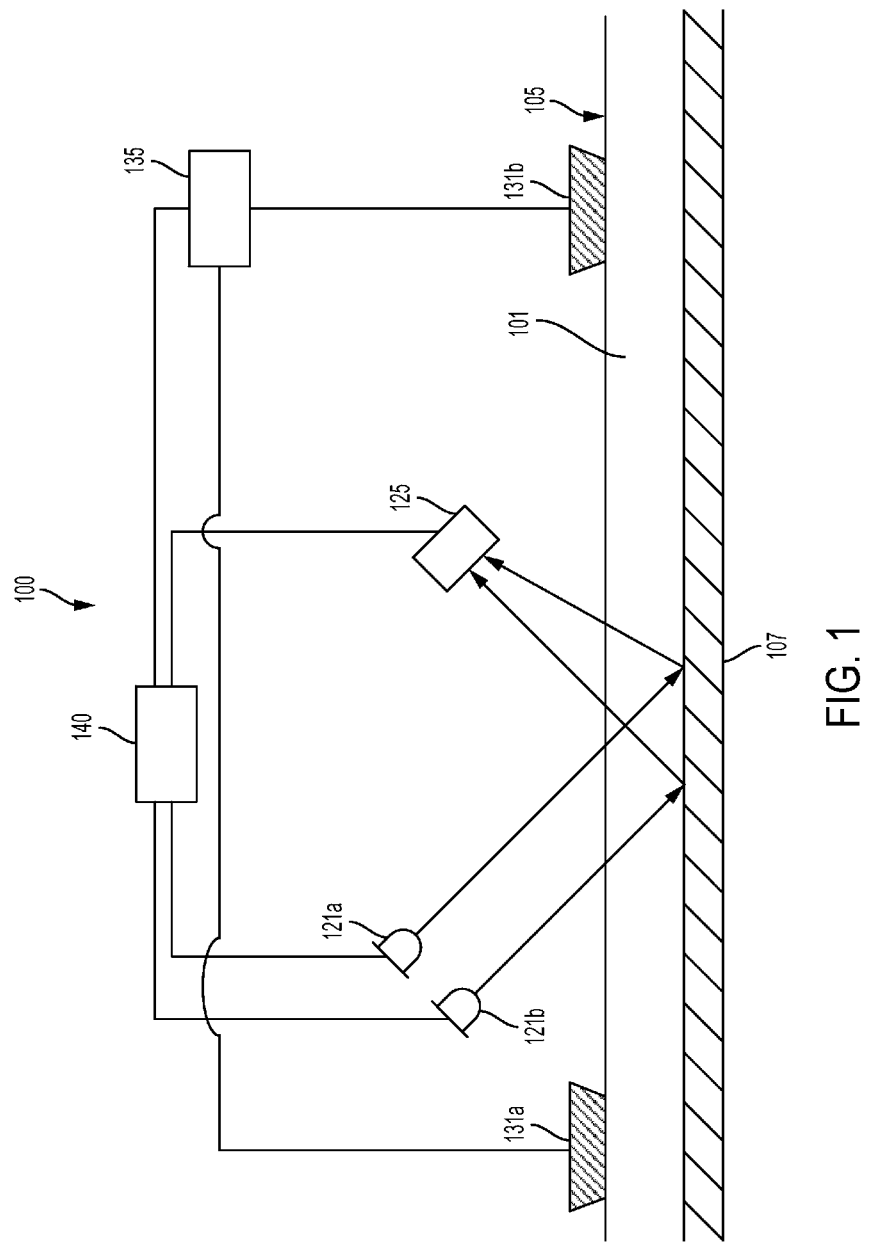
FIG. 1 is a schematic diagram of an example wearable device mounted to a skin surface.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use of devices and systems configured for use on or in conjunction with a living human body, it is contemplated that the disclosed methods, systems and devices may be used for any devices configured to be used in or proximate to an animal body, a natural environment (e.g., a river, a stream), an artificial environment (e.g., a food processing environment, a drug synthesis environment), or some other environment where samples of two or more signals can be generated using a multiplexer and an analog-to-digital converter such that a temporal relationship between samples of the two or more signals can be specified.

I. OVERVIEW

A wearable device may be configured to perform a variety of different functions and/or applications. In some examples, a wearable device is configured to measure one or more physiological properties of a wearer and/or to measure one or more properties of the environment of the wearer. For example, a wearable device could be configured to detect a pulse rate, blood flow rate or velocity, blood oxygenation level, blood pressure, arterial stiffness, pulse transit time, or some other hemodynamic properties of a portion of subsurface vasculature, a heart, blood, or some other element(s) of the cardiovascular system of a person. This could include detecting and/or determining one or more hemodynamic properties by detecting one or more related physical variables. For example, a pulse rate could be determined based on a detected intensity of light received from a portion of subsurface vasculature (related, e.g., to the volume of blood in the portion of subsurface vasculature over time) and/or based on a detected biopotential between two or more electrodes in contact with a skin surface (related, e.g., to the electrical activity of the heart, e.g., an electrocardiogram).

In some examples, a time difference or other properties of a temporal relationship between two or more different detected variables (e.g., a detected light intensity and a detected biopotential voltage) could be determined and used to determine hemodynamic or other physiological properties of a person (e.g., a pulse transit time, a blood pressure, an arterial stiffness). In such examples, a single analog-to-digital converter (ADC) could be used to digitize each of the two or more detected variables such that a temporal relationship between the detected variables (e.g., a relative timing between samples of the detected variables) can be controlled, known, or otherwise determined. In such examples, a multiplexer could be connected to the ADC and to two or more sensors or other elements configured to produce electrical signals corresponding to the two or more detected variables. The multiplexer and ADC could be operated to alternatively produce samples of the two or more detected variables or to produce samples of the two or more detected variables according to some other pattern.

In some examples, the multiplexer and ADC could be operated during a first plurality of specified periods of time (e.g., a first plurality of sampling times/periods) to generate a first plurality of digital codes (e.g., samples) of a first detected variable (e.g., an intensity of light received from a portion of subsurface vasculature that is related to, e.g., a volume of blood in the portion of subsurface vasculature). The multiplexer and ADC could be operated during a second plurality of specified periods of time (e.g., a second plurality of sampling times/periods that are offset in time from the first plurality of specified periods of time by a specified time difference) to generate a second plurality of digital codes (e.g., samples) of a second detected variable (e.g., a voltage between two electrical contacts that is related to, e.g., an electrocardiogram). Use of a single ADC to generate samples related to each of two or more detected variables could allow such samples to have a known relationship in time, e.g., related to a difference between the timing of the samples, to a latency between the detected variable(s) and related electrical, optical, or other signals detected by respective sensor(s), or other factors.

An oscillator (e.g., a digital clock) or other component(s) could be used to generate timing information used to control the timing of samples that are generated by an ADC and that are related to two or more detected signals. For example, such timing information could be used to clock a sample-and-hold, a sigma-delta modulator, a one-bit digital-to-analog converter, or other elements of the ADC such that digital codes generated by the ADC correspond to the values of detected variables and/or electrical signals related thereto during specified periods and/or points of time. Further, such timing information could be used to operate the multiplexer to connect signals from two or more sensors to the ADC. In some examples, this could include operating the multiplexer to connect an amplifier (e.g., a transimpedance amplifier) to two or more different sensors or other electronic components (e.g., preamplifiers, filters, buffers) corresponding to respective two or more different detected signals during respective different periods of time (e.g., respective different sampling periods or times). Further, such timing information could be used to operate some other elements of the wearable device, e.g., a light emitter configured to illuminate a portion of subsurface vasculature during a plurality of specified periods of time such that a corresponding light sensor (e.g., a photodiode, phototransistor, or other type of photodetector) can operate to detect light transmitted though, reflected by, scattered by, or otherwise emitted from the portion of subsurface vasculature during the plurality of specified periods of time (e.g., to generate a photoplethysmographic signal related to the volume of blood in the portion of subsurface vasculature).

The multiplexer could be configured to selectively connect a number of different electrical signals and/or components (e.g., the output of an electrocardiogram sensor, an output of a photodiode or other type of photodetector) to an ADC. In some examples, the multiplexer could be configured to connect such electrical signals and/or components to the input of an amplifier that has an output that is connected to the ADC. Such an amplifier could be a transimpedance amplifier, e.g., a transimpedance amplifier configured to apply a specified voltage to a photodiode and to output an electrical signal (e.g., a voltage) related to the current passing though the photodiode. Such an amplifier could be provided in a single integrated circuit with the ADC and/or the multiplexer. Such an integrated circuit could provide further components/functions, e.g., could include a timing generator (e.g., a digital oscillator) configured to generate timing information used to control the timing of samples that are generated by the ADC, the operation of the multiplexer, the illumination of the portion of subsurface vasculature by one or more light emitters, the operation of an electrocardiogram sensor, or the operation of some other components.

In some examples, a wearable device as described herein could include multiple light emitters configured to illuminate a portion of subsurface vasculature with illumination of respective different wavelengths during respective first and second pluralities of specified time periods. A photodetector (e.g., a photodiode) could be operated to detect light responsively emitted from the portion of subsurface vasculature during the first and second pluralities of specified time periods and such detected intensities could be used to detect hemodynamic properties, e.g., pulse rates, blood oxygenation levels, blood flow rates, or other properties. An ADC and multiplexer could be operated during the first and second pluralities of specified time periods to generate digital codes related to an output of the light sensor. Further, the ADC and multiplexer could be operated during a third plurality of specified time periods to generate digital codes related to an output of an electrocardiogram sensor (e.g., two or more electrical contacts and amplifier(s), buffer(s), filters, or other associated components). For example, the ADC and multiplexer could be operated to alternate between generating digital codes related to the output of the electrocardiogram sensor, the output of the light sensor when the portion of subsurface vasculature is being illuminated by the first light emitter, and the output of the light sensor when the portion of subsurface vasculature is being illuminated by the second light emitter. The ADC and multiplexer could be operated to generate digital codes related to further variables and/or signals during further specified periods of time, e.g., related to the output of the light sensor during periods of time when the portion of subsurface vasculature is not being illuminated by the wearable device (e.g., to detect an ambient light level).

In some examples, the wearable device may include a user interface that is configured to provide user-discernible indications (e.g., visual, audible, and/or tactile indications) of information sensed by sensors of the wearable device, progress or other information related to a function of the device, or other information. In some examples, the user interface could additionally provide a means for one or more settings of the wearable device (e.g., a sampling rate, a user information privacy setting, a user's credentials to access a service) to be specified by a wearer according to the wearer's preferences. Indications provided by an output component (e.g., a display, a beeper, a vibrator, a speaker) could indicate information related to a detected hemodynamic property or other physiological property, e.g., a determined heart rate, a determined pulse transit time, a determined blood oxygen saturation, a determined blood pressure. In some examples, the wearable device may include a wireless communication interface that can transmit/receive data to/from an external device, for example, using Bluetooth, ZigBee, WiFi, and/or some other wireless communication protocol. The wireless communications interface could additionally or alternatively be configured to receive data from an external system (e.g., parameters relating to the operation of an energy emitter configured to emit energy into blood of the wearer to effect a change in some analyte in the blood).

The wearable device could include a mount (e.g., a strap, a belt, an enclosing member, an adhesive) configured to secure the wearable device to a wrist, neck, abdomen, ankle, or some other location of a user's body. Additionally or alternatively, embodiments described herein could be configured as other types of devices, e.g., handheld devices, benchtop devices, or otherwise configured devices. Devices as described herein (e.g., wearable devices) could be configured to removably couple to external systems, e.g., external chargers, to provide a variety of applications. For example, an external charger could provide power (e.g., power to recharge a battery of a wearable device), communications (e.g., a communications channel to download updated software, to upload recorded information, to interact with a vehicle), or some other facilities to the wearable device.

As used herein, the word 'electrocardiogram' refers to aspects of detected biopotentials (e.g., voltages detected between two or more locations of a body, first and second location of skin on the chest of a body, first and second locations on first and second arms of a body, some other locations on or within a body) that are related to the electrical activity of the heart of a body. In some examples, a detected electrocardiogram could include additional components related, e.g., to the electrical activities of muscles, nerves, electromagnetic fields in the environment of a body (related, e.g., to electrostatic discharges, current flows in electronic equipment, current flows in the wiring or a building), or other sources of electrical fields or currents on or around a body. A detected electrocardiogram may include a detectable QRS complex, a P wave, or other features or may lack such features, or may include other features. Properties of a detected electrocardiogram may be related to means used to detect the electrocardiogram (e.g., electrical properties of electrodes and/or of the electrical interface between such electrodes and tissues of a body, the location of such electrodes on or within a body, properties of an electrocardiogram sensor configured to detect the electrocardiogram using such electrodes), tissues interposed between such means and the heart (e.g., a conductivity, geometry, or other properties of an abdomen, limbs, head, skin, or other tissues), or other factors.

It should be understood that the above embodiments, and other embodiments described herein, are provided for explanatory purposes, and are not intended to be limiting.

II. EXAMPLE DETECTION OF HEMODYNAMIC PROPERTIES

A variety of physiological parameters of a body (e.g., a blood pressure, a pulse transit time, a blood oxygenation, a stiffness of a blood vessel) can be determined based on two or more detected physical variables. For example, a blood oxygenation can be determined based on a relationship (e.g., a ratio) between the absorption of light at two or more different wavelengths by blood in a portion of arterial subsurface vasculature. In some examples, such physiological parameters can be determined based on a time difference between corresponding features (e.g., maxima, minima, features) or other properties of first and second (or more) detected physical variables (e.g., physical variables detected by respective different sensors of a system or device).

Such a time difference could be related to the duration, speed, or other properties of a process or operation of the body. In such examples, a detected time difference could be used to determine one or more properties of the process of operation, e.g., to determine the duration of a heartbeat from initiation at the atrial node to the final ejection of blood from the heart. Additionally or alternatively, such a time difference could be related to the time it takes for a signal, pressure wave, fluid flow, or other process or material to propagate from a first location to a second location (e.g., the time it takes for a pressure wave generated by the heart during a heartbeat to travel from the heart to a portion of subsurface vasculature). In such examples, a detected time difference could be used to determine properties of the tissues involved in the propagation (e.g., a stiffness of one or more portions of vasculature, a pressure and/or pressure waveform of blood involved in the propagation, or an action potential velocity of a nerve).

Such time differences could be determined based on one or more physical variables detected at two or more locations, e.g., detecting a volume of blood in two or more portions of subsurface vasculature through which blood flows from the heart to peripheral tissues. In an example, the velocity of a pressure wave in blood could be determined based on the detected volume of blood in upstream and downstream portions of an artery in the arm of a user (detected, e.g., by illuminating the upstream and downstream portions and detecting a change in the absorption of the illumination over time). The detected physical variable (e.g., an intensity of light emitted from a portion of subsurface vasculature responsive to illumination, a voltage between two locations of a skin surface, a displacement and/or force exerted at a skin surface) at the two or more locations could be the same physical variable (e.g., a detected light intensity at upstream and downstream locations) or different physical variables (e.g., a pressure, force, or displacement at a first location and an intensity of light at a second location).

Such time differences could be determined based on two or more physical variables detected at substantially the same location. In some examples, the timing of features of one or more of such detected physical variables could be related to processes proximate the location of detection. For example, a flow rate and volume of blood in a particular portion of subsurface vasculature could be detected based on, respectively, a time-varying pattern of constructive and destructive interference in light received from the portion of subsurface vasculature and an intensity of light received from the portion of subsurface vasculature. Additionally or alternatively, the timing of features of one or more of such detected physical variables could be related to processes distant from the location of detection. For example, a timing of electrical activities of the heart (e.g., electrical activities related to the contraction of the ventricles and/or atria of the heart to pump blood during a heartbeat) could be detected based on a voltage (e.g., a biopotential) detected between two skin locations (e.g., two locations on a wrist, a location on a wrist and a location on a finger or other skin of an arm opposite the arm of the wrist).

As an example, FIG. 1A shows a schematic view of elements of a device 100 having elements mounted proximate to and/or in contact with an external body surface 105 of skin 101 of a person (e.g., a wrist surface of an arm). A portion of subsurface vasculature 107 is disposed beneath the external body surface 105. Two electrical contacts 131a, 131b are mounted to respective locations on the external body surface 105 and are configured to electrically connect with the skin 101 to provide functions of the device 100 (e.g., to detect a property, e.g., a Galvanic skin resistance, a biopotential related to an electrocardiogram, of skin 101 to which the electrical contacts 131a, 131b are exposed). The electrical contacts 131a, 131b are connected to an electrocardiogram (ECG) sensor 135 that is configured to detect an electrocardiogram using the electrical contacts 131a, 131b. First 121a and second 121b light emitters are configured to illuminate the portion of subsurface vasculature 107 with respective lights having respective properties (e.g., respective different wavelengths). A photodetector 125 is configured to detect one or more properties (e.g., an intensity) of light emitted by (e.g., scattered by, reflected by, refracted by, fluorescently emitted by) the portion of subsurface vasculature 107 responsive to illumination by one or both of the lithe emitters 121a, 121b. A controller 140 is provided to operate the light emitters 121a, 121b, photodetector 125, and ECG sensor 135 to provide operations of the device 100, e.g., to detect physiological parameters of a user to whose skin 101 the elements of the device are mounted.

The device 100 could be provided as a wearable device (e.g., including a mount configured to secure the electrical contacts 131a, 131b, light emitters 121a, 121b, and photodetector 125 proximate the portion of subsurface vasculature 107 and/or external body surface 105). Alternatively, the device 100 could be configured in some other way, e.g., as a handheld, tabletop, wall-, floor-, or ceiling-mounted device, or configured in some other way. A wearable device can be any device configured to be mounted to a body and to provide some functions of the wearable device. Such a device could include a mount, a strap, adhesives, could be incorporated into a garment, or include other means or be otherwise configured to be mounted to a body, e.g., to a skin surface of a body. For example, a wearable device could be configured to be mounted to a wrist of a body. A wearable device could include a user interface and/or communications means (e.g., a Bluetooth radio, a WiFi radio) configured to indicate information to a user and/or to receive inputs from a user, to communicate information with an external system, or to provide other functions. For example, a communications interface of the wearable device could be configured to receive notifications from an external system (e.g., a cellphone) and to indicate those notifications using a display. Such a display could additionally be used to provide indications of information (e.g., pulse rates, blood oxygen saturations, pulse transit times) detected using sensors of the wearable device.

Note that the configuration of the device 100 (that is, the location of electrical contacts 131a, 131b near an external body surface 105 of skin 101 that is proximate a portion of subsurface vasculature 107 being illuminated by the light emitters 121a, 121b and from which the photodetector 125 is detecting emitted light) is intended as an illustrative example of the systems and methods described herein. A device (e.g., a wearable device) configured to optically, electrically, and/or otherwise detect physical variables and/or physiological parameters of a body could be differently configured and/or could include more or fewer of the illustrated elements. For example, the electrical contacts 131a, 131b could be configured to electrically contact respective skin locations that are not proximate the portion of subsurface vasculature 107 being optically interrogated by the light emitters 121a, 121b and photodetector 125, e.g., locations on the chest, arms, or other locations of a body.

In some examples, a first electrical contact (e.g., 131a) could be configured to electrically contact skin proximate the portion of subsurface vasculature 107 being optically interrogated by the device 100 and the other electrical contact (e.g., 131b) could be configured to electrically contact skin that is distant from the portion of subsurface vasculature 107. For example, the second electrical contact could be mounted to a distal location of a body and could be connected to the ECG sensor 135 via a wire. In some examples, the second electrical contact could be configured to be contacted by skin at the second location. The first electrical contact could be configured to contact skin at a wrist of first arm of a wearer (or some other location to which the device 100 is mounted) and the second electrical contact could be configured to be contacted by skin of a finger, hand, or other location of a second arm of the wearer.

In some examples, the device 100 could include a third electrical contact (not shown) that is connected to the ECG sensor 135 and that is configured to be mounted to the skin 101 at a third location. The ECG sensor 135 could be configured to drive the third electrical contact according to an average of the signals present at the first and second electrical contacts, e.g., to reduce a common-mode signal present at the first and second electrical contacts. That is, the ECG sensor 135 could use the third electrical contact to reduce a voltage difference between the device 100 (e.g., a ground of the device, the first and second electrical contacts of the device) and the skin 101.

The disposition of sensors, electrical contacts, user interface elements (e.g., displays, buttons, touch-sensitive elements), or other components of devices (e.g., 100) as described herein could be specified to allow sensors to access portions of the body, to permit a user to comfortably provide inputs to the device, to permit the user to see a display or otherwise receive an indication provided by the device, or to provide some other application. For example, a wearable device could be configured to be mounted to a wrist of a wearer. A display and/or other elements of a user interface of such a device could be disposed on/within the device such that the wearer can easily view the display and/or interact with the user interface when the device is mounted to the user's wrist. Further, sensors of such a wearable device could be disposed on or within the device to detect physiological parameters of the body, e.g., to optically interrogate a portion of subsurface vasculature within the wrist, to detect an electrocardiogram using one or more electrical contacts in electrical contact with skin of the wrist, or to operate some other sensors when the device is mounted to the user's wrist. Such a wrist-mounted wearable device could detect an electrocardiogram by detecting a voltage between two or more skin locations of the wrist. Additionally or alternatively, a wrist-mounted wearable device could detect a voltage between a skin location of the wrist and some other skin location that is electrically accessible to and/or made accessible to the wrist-mounted device (e.g., via a wire connecting the device to an electrical contact at some other skin location, via a wearer placing skin of a finger or some other body part in contact with an electrical contact of the wrist-mounted device).

Embodiments of systems or methods described herein could include a variety of types of sensors configured in a variety of ways to detect a variety of different physiological and/or environmental properties according to an application. Sensors could be configured to be in electrical, thermal, mechanical, fluidic, chemical, or some other form of contact or access with tissues of a body. This could include a sensor having one or more electrodes or probes having a specified electrical, thermal, or other resistance and configured to allow a flow of heat energy, electrical current, or some other energy through the electrodes or probes. In some examples, a sensor could include two or more electrodes configured to allow a voltage between two or more respective portions of tissue in contact with the electrodes to be measured, to allow a current through the two or more electrodes to be measured, to allow a current and/or voltage to be provided to the portions of tissue, or to allow some other electrical interaction with tissue. In some examples, one or more electrical contacts (e.g., 131a, 131b) of the device could be configured to electrically connect with electrical contacts of an external charger (or other external device).

Sensors could be configured to emit energy toward/into portions of tissue (e.g., portions of subsurface vasculature) and/or to receive energy emitted from portions of tissue to allow detection of hemodynamic parameters or other properties of a body. Sensors could be configured to emit and/or receive light (e.g., visible, infrared, or ultraviolet light), electromagnetic radiation, acoustical vibrations (e.g., pulses of ultrasound), electrical fields, magnetic fields, or some other directed energy or energy field(s). In such examples, one or more properties or features of an excitation spectrum, an abruption spectrum, an emission spectrum, a scattering spectrum, or some other optical property of tissues (e.g., of blood within a portion of subsurface vasculature) or of some other environment of interest could be detected.

To determine a time difference between corresponding features or other properties of first and second (or more) detected physical variables, a device (e.g., 100) could sample signals related to the first and second detected physical variables during a plurality of different periods of time (e.g., a plurality of different sampling periods or times). Sampled values of the signals could be analyzed to determine timing information (e.g., the timing of maxima, minima, or other features of each of the detected physical variables) of features within the sampled values of each signal. A time difference between the features of the detected signals could be determined based on the determined timing of features within the sampled values and the relative timing of the sampled values (e.g., based on the relative timing of each of the periods of time during which the sampled values were generated).

In some examples, this could include operating one or more analog-to-digital converters (ADCs) and/or other signal processing components (e.g., amplifiers) to generate digital codes based on each of the signals of interest. For example, first and second ADCs (and corresponding first and second amplifiers, buffers, or other elements) could be used to generate respective pluralities of digital codes based on signals related to respective first and second detected physical variables (e.g., a first signal related to the intensity of light received from a portion of subsurface vasculature and a second signal related to a detected electrocardiogram). Such multiple (e.g., first and second) ADCs could generate digital samples at substantially the same frequency and/or relative timing (e.g., a plurality of specified periods of time during which the first ADC generates digital codes could be substantially the same as a plurality of specified periods of time during which the second ADC generates digital codes). Alternatively, such multiple ADCs could operate to generate digital codes at different frequencies or according to some other pattern that differs between the multiple ADCs.

In some examples, a multiplexer could be used to selectively connect multiple signals related to respective physical variables to a single ADC and related signal-processing components (e.g., an amplifier, a buffer, a filter). The ADC could be operated, in combination with the multiplexer, to generate multiple pluralities of digital codes based on the signals related to respective physical variables. In such an example, the use of a single ADC to generate digital codes for multiple different signals could provide control of the relative timing between generated digital codes based on the different signals. For example, the multiplexer and ADC could be operated such that a sequence of digital codes generated by the ADC correspond, alternatingly, to first and second signals alternatively electrically connected to the ADC via the multiplexer. Such different signals could correspond to the outputs of multiple different sensors (e.g., the output of a photodetector and the output of an ECG sensor), outputs of a single sensor when exposed to a different condition or environment (e.g., the output of a photodetector when a target environment of the photodetector is illuminated by different light sources with light of different wavelengths and/or by ambient light sources) or some combination thereof.

Figure 2:
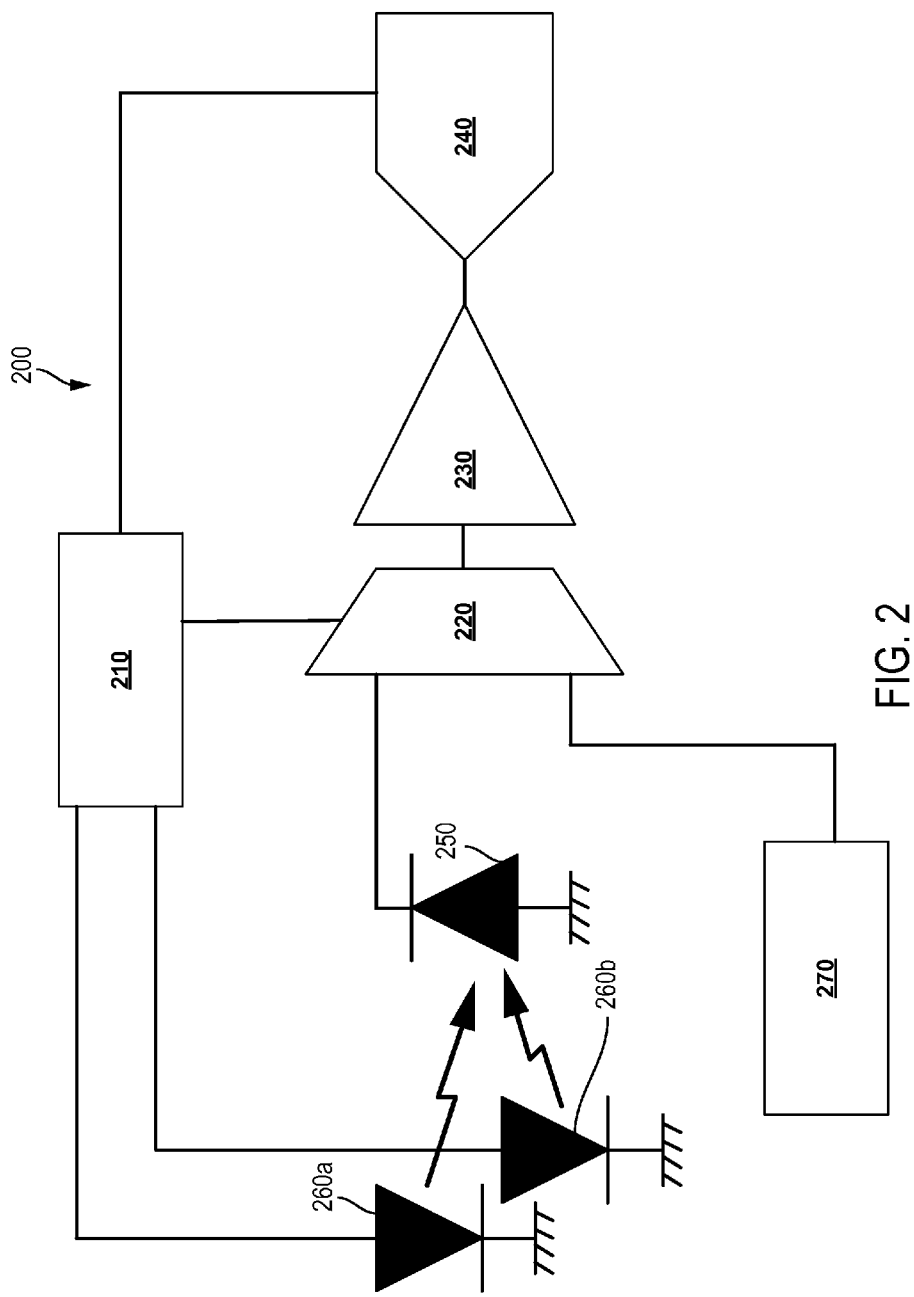
FIG. 2 is an example schematic of circuitry of a system configured to detect optical and electrocardiographic signals.

FIG. 2 illustrates an example circuit 200 for generating digital codes based on multiple signals using a single ADC 240. The circuit 200 includes a photodiode 250 and an electrocardiogram (ECG) sensor 270 connected to inputs of a multiplexer 220. The multiplexer is configured to selectively connect the output of one of the photodiode 250 and ECG sensor 270 to an input of an amplifier 230. The amplifier 230 is connected to the ADC 240 such that the ADC 240 can be operated to generate digital codes based on the output of the amplifier 230. The ECG sensor 220 is configured to detect an electrocardiographic signal via an external body surface. The photodiode 210 is configured to receive (e.g., via the external body surface) light emitted from (e.g., reflected by, scattered by) a portion of subsurface vasculature in response to illumination by one or more of first 260a and second 260b light emitters. A controller 210 is provided to operate the light emitters 260a, 260b, multiplexer 220, and ADC 240.

The ECG sensor 270 is configured to detect a time-varying voltage between two points on the external body surface (that is, skin) that is related to the electrical activity of the heart. The ECG sensor 270 includes two electrical contacts or electrodes configured to be mounted to an electrically couple with the two points on the external body surface. This could include coupling to the skin capacitively (e.g., by including a thin layer of a dielectric or other nonconductive material that can be mounted in contact with the skin), ohmically (e.g., by being composed in whole or in part by gold, silver/silver chloride, or some other metal or other conductive material), or in some other way such that voltages and/or currents produced by electrical activity of the heart can be detected using the electrical contacts or electrodes. The two points could be points on the chest, arms, legs, head, or other locations of the body. For example, the electrodes could be disposed on a wrist-mountable device such that a first electrode is mounted to, and in electrical contact with, skin of the wrist when the device is mounted to the wrist. A second electrode could be disposed on the device such that a wearer could contact the second electrode with a finger or other elements of the arm opposite the arm to which the device is mounted.

The ECG sensor 270 could include buffers, instrumentation amplifiers, filters, coupling capacitors, operational amplifiers, or other elements configured to generate a signal related to the electrical activity of the heart using two or more electrodes in contact with respective locations on the external surface of a body. The output of the ECG sensor 270 could have a specified offset and/or dynamic range and such a specified offset and/or dynamic range could be specified based on corresponding properties of the amplifier 230 and/or ADC 240. Further, a gain, offset, filter cutoff, or other properties of the ECG sensor 270 could be controllable (e.g., based on an amplitude of a detected electrocardiogram to prevent saturation of the amplifier 230). Further, the ECG sensor 270 could include means for detecting an impedance and/or capacitance between two or more electrical contacts. Such a detected impedance and/or capacitance could be used to determine whether the electrical contacts are mounted to external body surfaces such that an electrocardiogram can be detected. Further, the ECG sensor 270 could be operated based on such a determination, e.g., to disable the ECG sensor, to blank the output of the ECG sensor, or to perform some other function in response to the determination that the electrical contacts are not mounted to an external body surface.

The multiplexer 220 could include one or more electronic switches (e.g., bipolar transistors, field-effect transistors) that are operable to, during respective different periods of time, connect the different outputs of the photodiode 250 and ECG sensor 270 to the input of the amplifier 230. Such switching could include connecting a single electrical signal from the output of one of the signal sources to the amplifier 230. That is, the outputs could be single-ended electrical signals that are referenced to a specified ground signal. Additionally or alternatively, such switching could include connecting two or more electrical signals from the output of one of the signal sources to the amplifier 230. That is, the outputs could include two electrical signals such that the output of the signal source comprises the difference between the two electrical signals. Such switching could additionally include connecting the output(s) of non-selected signal sources (e.g., the ECG sensor 270) to a specified impedance or other signal sink or other component(s). For example, the multiplexer 220 could connect the output of the ECG sensor 270 to a specified impedance when the output of the ECG sensor 270 is not connected to the amplifier 230 to save power, such that the output of the ECG sensor 270 does not oscillate, such that an output stage of the ECG sensor 270 does not saturate, or according to some other consideration.

The multiplexer could have a specified maximum leakage current, e.g., to prevent cross-talk between the two or more signal sources and/or to prevent cross-talk between such a signal source and the amplifier 230 when the signal source is not selected. For example, the multiplexer 220 could have a leakage current that is less than approximately 1 nanoamp.

The amplifier 230 could include a variety of different components (e.g., transistors, operational amplifiers, active or passive filters, level shifters, buffers) configured to provide an output electrical signal to the ADC 240 that is related to a signal received from the photodiode 250, ECG sensor 270, or some other signal source via the multiplexer 220. This could include applying a gain, an offset, or some other relationship between a property of a received signal (e.g., the magnitude of a current received by the amplifier 230 via the multiplexer 220) and a generated signal (e.g., the magnitude of a voltage or current) that is applied to an input of the ADC 240. For example, the amplifier 230 could be configured to apply a gain and offset to a received input signal such that a generated signal applied to the ADC 240 has values within a dynamic range of the ADC 240. In some examples, the output of the amplifier 230 could have a nonlinear relationship with the input of the amplifier 230, e.g., to provide a degree of amplitude compression to signals received through the multiplexer 230, to prevent saturation of the amplifier 230, or according to some other consideration.

In some examples, the amplifier 230 could be a transimpedance amplifier that is configured to apply a specified reverse bias voltage to the photodiode 250 and to generate an output signal related to the magnitude of current through the photodiode 250 when the multiplexer 220 is connecting the output of the photodiode 250 to the amplifier 230. Alternatively, the photodiode 250 could be replaced with some other photodetector, e.g., a phototransistor. In such examples, the ECG sensor 270 could include an amplifier or other components configured to generate an output voltage related to (e.g., equal to an amplified and/or filtered version of) a biopotential measured using electrical contacts between two locations of an external body surface (e.g., first and second skin locations on a wrist of a person). The output voltage signal could be connected to the multiplexer 220 via a resistor such that the output of the transimpedance amplifier 230 is an amplified version of the output voltage signal scaled by an amount related to the gain of the transimpedance amplifier 230 and the value of the resistor. Further, the output voltage signal could be connected to the multiplexer 220 via a blocking capacitor, e.g., to prevent large-amplitude DC components of the biosignals detected by the ECG sensor 270 from being amplified by the amplifier 230.

The ADC 240 is configured to generate digital codes (e.g., digital codes representing binary digital values) related to electrical signals received from the amplifier 230. The generated digital codes could represent binary values, delta modulated bit streams, or could have other relationships to the voltage, current, or other properties of signals received from the amplifier 230 at and/or during one or more points and/or periods of time. The ADC 240 could include one or more comparators, oscillators, sample-and-holds, integrators, digital switches, differentiators, amplifiers, operational amplifiers, digital-to-analog converters, sigma-delta modulators, or other components configured as a flash ADC, an integrating ADC, a successive-approximation ADC, a pipelined ADC, a sigma-delta ADC, or in some other way to generate a plurality of digital codes based on an electrical signal received via the multiplexer 220 during respective sampling times or sampling periods.

The ADC 240 could be configured to produce digital codes having a specified resolution, e.g., digital codes having a resolution of 22 bits. For example, the ADC 240 could be a sigma-delta ADC configured to generate a delta-modulated stream of bits based on the magnitude of signals received by the ADC 240. Such an ADC could further include a decimator and digital demodulator configured to generate digital codes based on the generated delta-modulated bit stream (e.g., by counting a number of '1'-valued bits within a specified sequence of bits bit stream). The frequency of the delta-modulated stream of bits and the configuration of the decimator and digital demodulator could be specified such that the ADC 240 generates digital codes having a specified resolution or bit width (e.g., a bit width greater than approximately 22 bits) at a specified frequency (e.g., a frequency of greater than approximately 400 Hertz).

The first 260a and second 260b light emitters are configured to illuminate a portion of subsurface vasculature with respective different lights (e.g., lights differing according to wavelength, spectral content, degree and/or direction of polarization) such that the photodiode 250 can receive light responsively reflected by, scattered by, fluorescently re-emitted by, or otherwise emitted from the portion of subsurface vasculature responsive to illumination by the light emitters 260a, 260b. The light emitters 260a, 260b could include LEDs, lasers, or some other light-emitting components. The light emitters 260a, 260b could include filters, gratings, mirrors, lenses, or other optical elements configured to control a wavelength, spectrum, coherence length, focal length, beam width, angle, or other properties of light emitted from the light emitters 260a, 260b.

The controller 210 is configured to operate the elements of the circuit 200. This includes driving the light emitters 260a, 260b during respective first and second pluralities of specified periods of time to illuminate the portion of subsurface vasculature. This could include operating constant-current drivers to apply specified amounts of current to each of the light emitters 260a, 260b during the first and second pluralities of specified periods of time. The amounts of current applied to the light emitters 260a, 260b could be specified such that the intensity (or some other property) of the light responsively emitted from the portion of subsurface vasculature is within a specified range of values. For example, the amounts of current applied to the light emitters 260a, 260b could be specified such that the signal output from the photodiode 250 responsive to the resulting illumination emitted from the light emitters 260a, 260b is, after amplification by the amplifier 230, within a dynamic range of the ADC 240.

The controller 210 operating elements of the circuit 200 further includes operating the multiplexer 220 to selectively connect the output of the photodiode 250 to the input of the amplifier 230 during the first and second pluralities of specified periods of time and to selectively connect the output of the ECG sensor 270 to the input of the amplifier 230 during a third plurality of specified periods of time. Further, the controller 210 is configured to operate the ADC 240 to generate first, second, and third pluralities of digital codes based on signals received from the amplifier 230 during specified time periods of the first, second, and third pluralities of specified time periods. This could include providing a clock signal, timing signals, configuration information, or otherwise controlling the operation of the ADC 240. Operating the ADC 240 to generate first, second, and third pluralities of digital codes additionally includes receiving the generated digital codes.

The controller 210 can be configured to perform additional operations. For example, the controller 210 could be configured to determine hemodynamic and/or physiological parameters of a human body based on pluralities of digital codes generated by the ADC 240. For example, a pulse rate, pulse timing, pulse variability, or other properties of the activity of the heart could be determined based on a plurality of digital codes generated by the ADC 240 based on one or more of the signals input into the multiplexer 220 (e.g., an electrocardiogram signal, a photoplethysmogram signal associated with illumination of a portion of subsurface vasculature by one of the light sources 260a, 260b). This could include determining the timing of maxima, minima, peaks, or other features within a particular plurality of generated digital codes.

In some examples, the controller 210 could determine a hemodynamic or other parameter of the body based on multiple pluralities of generated digital codes corresponding to respective different detected signals. For example, the controller 210 could determine an oxygen content of blood in a portion of subsurface vasculature based on a ratio, difference, or other relationship between values of first and second pluralities of digital codes corresponding to outputs of the photodiode 250 when the portion of subsurface vasculature is illuminated by the first 260a and second 260b light sources, respectively. In another example, the controller 210 could determine a pulse transit time, an arterial stiffness, a blood pressure, or some other hemodynamic parameters based on first and second pluralities of digital codes corresponding to outputs of the photodiode 250 and ECG sensor 270, respectively. This could include determining a time difference between the timing of a feature in a detected electrocardiogram (e.g., by detecting the feature in a corresponding plurality of digital codes generated during specified period of time when the multiplexer 220 is connecting the ECG sensor 270 to the amplifier 230) and the timing of a corresponding feature in a detected photoplethysmogram (e.g., by detecting the feature in a corresponding plurality of digital codes generated during specified period of time when the multiplexer 220 is connecting the photodiode 250 to the amplifier 230 and the portion of subsurface vasculature is being illuminated by a particular one of the light emitters 260a, 260b). The controller 210 could be configured to determine other hemodynamic and/or physiological parameters or other information based on digital codes generated by the ADC 240 and/or other information sources.

One or more elements of the circuit 200 and/or elements of the illustrated components (e.g., a counter, digital oscillator, constant-current driver, or other aspects of the controller 210) could be implemented in a single integrated circuit. For example, the amplifier 230 and ADC 240 could be provided in a single integrated circuit. Further, such an integrated circuit could include constant-current drivers or other elements configured to control a timing and/or current applied to one or both of the light emitters 260a, 260b. Such an integrated circuit could additionally include digital counters, oscillators, or other elements configured to control the timing of the operation of the multiplexer 220 to connect signals to the amplifier 230, the timing of the ADC 240 to generate digital codes, or to control the timing of operation of additional components (e.g., to control a power state of the ECG sensor 270).

Figure 3A:
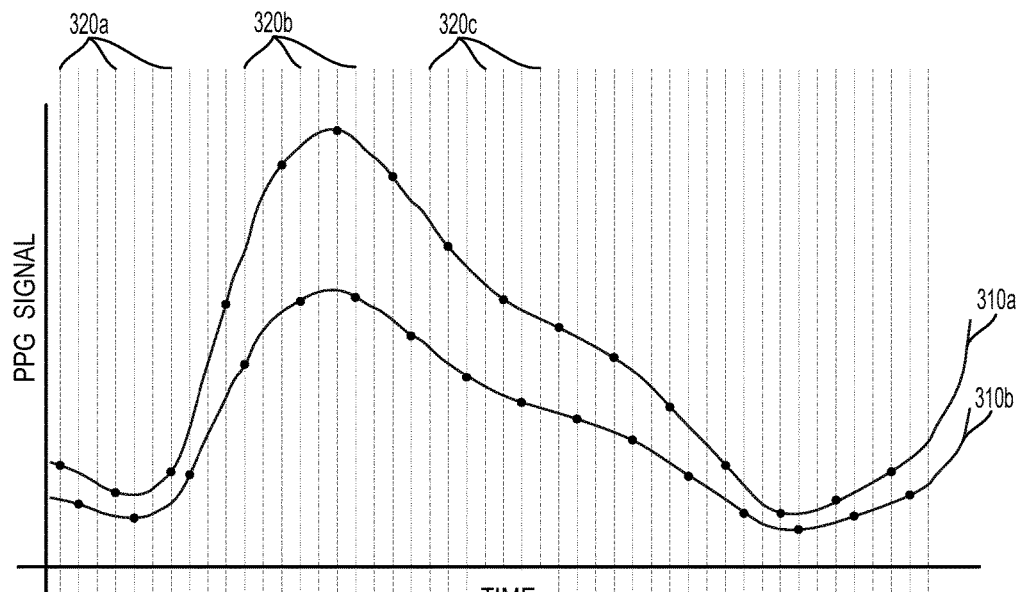
FIG. 3A illustrates example signals generated by a photodetector and the timing of samples of the example signals.
Figure 3B:
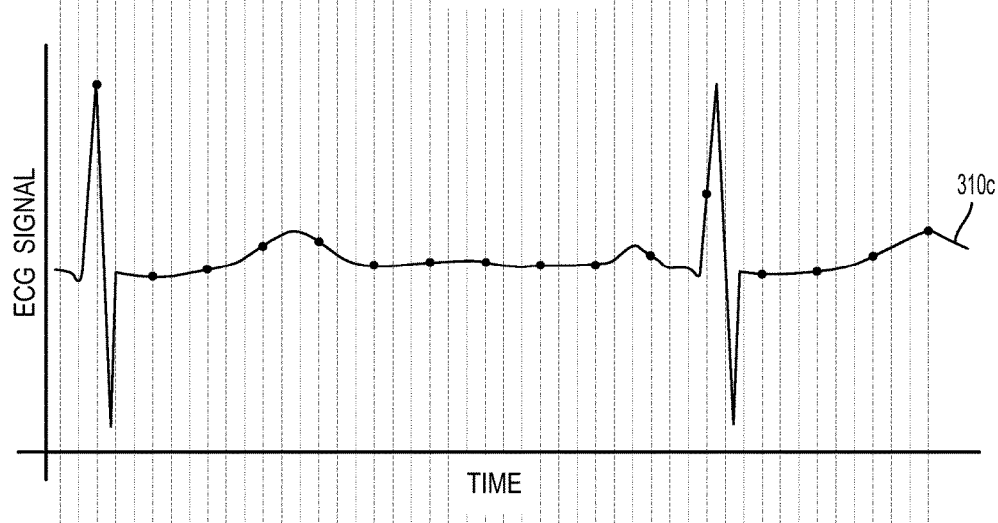
FIG. 3B illustrates an example signal generated by an electrocardiogram sensor and the timing of samples of the example signal.

FIGS. 3A and 3B illustrate the generation of multiple pluralities of digital codes based on multiple respective physical variables (that is, based on detected signals related thereto) during respective pluralities of periods of time (e.g., pluralities of sampling times or periods). The illustrated signals could be signals generated by elements of the device 100 or the circuit 200 of FIGS. 1 and 2, respectively. FIG. 3A shows first 310a and second 310b photoplethysmogram waveforms over an example period of time. FIG. 3B shows an electrocardiogram waveform 310c over the same example period of time as illustrated in FIG. 3A. The vertical dashed lines indicate first, 320a, second 320b, and third 320c pluralities of specified periods of time, e.g., pluralities of sampling times during which an ADC and multiplexer could be operated to generate digital codes based on each of the photoplethysmograms 310a, 310b and electrocardiogram 310c, respectively.

The photoplethysmogram waveforms 310a, 310b correspond to an amount of light that a photodetector receives from a portion of subsurface vasculature in response to illumination by respective first and second light emitters that are configured to emit light at respective first and second wavelengths (e.g., at a red and a near infrared wavelength or at respective different green wavelengths). Changes over time of the light intensity waveforms 310a, 310b can be related changes in the volume of blood in the portion of subsurface vasculature. A difference (e.g., an arithmetic difference, a ratio) between the first 310a and second 310b light intensity waveforms can be related to a degree of oxygenation of blood in the portion of subsurface vasculature (e.g., to a relative absorption of oxygenated and deoxygenated hemoglobin in the blood at the first and second wavelengths of the light illuminating the portion of subsurface vasculature).

The electrocardiogram waveform 310c corresponds to a time-varying voltage between the external surface of a body at two locations (e.g., locations on the chest, first and second locations on respective first and second arms of a body). Properties of the electrocardiogram waveform 310c (e.g., the timing, frequency, shape, amplitude, or other properties of a peaks or other features of the waveform) can be related to properties and/or activity of the heart. For example, the timing of QRS complexes in the electrocardiogram waveform 310c can be related to the timing of beats of the heart.

Sampled values of the illustrated waveforms 310a, 310b, 310c are illustrated by filled dots located at times corresponding to respective pluralities of specified periods of time (320a, 320b, 320c). As illustrated, time periods of each of the three pluralities specified periods of time alternate. That is, a first digital code related to the first photoplethysmogram waveform 310a is generated during a first time period; a second digital code related to the second photoplethysmogram waveform 310b is generated during a second time period that is immediately subsequent to the first time period; and a third digital code related to the electrocardiogram waveform 310c is generated during a second time period that is immediately subsequent to the first time period. The first, second, and third time periods are specified time period of the first, second, and third pluralities of specified period of time, respectively. Further, the illustrated time periods have substantially similar durations, i.e., the generated digital codes are generated at a constant rate (e.g., approximately 300 Hz) such that digital codes corresponding to a particular one of the signals (e.g., 310a, 310b, 310c) are generated at substantially the same rate (e.g., approximately 100 Hz).

The timing of maxima, minima, peaks, or other features of each of the signals (e.g., 310a, 310b, 310c) can be determined based on the digital codes generated based on each of the signals. A difference in timing between such features (e.g., between a QRS wave in codes generated based on an electrocardiogram and a corresponding absorption maximum in codes generated based on a photoplethysmogram) can be determined based on the determined timings within the generated codes and the relative timing of generation of the digital codes. The use of a single ADC (and related components, e.g., an amplifier disposed between the multiplexer and the ADC) provides for a common latency between the timing of events in a signal (e.g., the timing of a peak or other feature) and the timing of a corresponding one or more digital codes. As a result, the relative timing of features within a set of generated digital codes could be determined based on the timing of operation of the single ADC to generate digital codes corresponding to the features.

Note that these properties of the signals and timing of corresponding generated digital codes, as shown in FIGS. 3A and 3B, are intended as non-limiting illustrative examples. A multiplexer, ADC, and other components (e.g., amplifiers, buffers, filters) could be used to generate, based on two or more signals, respective pluralities of digital codes according to some other pattern, sequence, or timing. In some examples, a particular signal could be sampled more frequently than another signal (e.g., the multiplexer and ADC could be operated to repeatedly generate a sequence of digital codes that includes four codes based on a first signal followed by a fifth code based on a second signal). For example, a first signal could include higher-frequency content than a second signal and the multiplexer and ADC could operate to generate digital codes based on the first signal more frequently. In some examples, the duration of the sampling times/period could differ. For example, the multiplexer and ADC could be operated to generate digital codes based on a first signal during first specified periods of time that are substantially longer than second specified periods of time during which the multiplexer and ADC operate to generate digital codes based on a second signal (e.g., due to a different settling time of an amplifier relative to the different signals, different integration times of an amplifier or ADC relative to noise properties of the different signals, or according to some other consideration).

The frequency at which the digital codes are generated and/or the frequency at which digital codes are generated based on a particular signal could be specified according to an application. In some examples, the signals could be related to the intensity of light received from a portion of subsurface vasculature by a photodetector (e.g., photoplethysmograms), signals related to a time-varying voltage between two points on an external body surface (e.g., electrocardiograms), or other signals related to hemodynamic parameters of a body. Such hemodynamic parameters include information related to properties and operation of the heart, blood, vasculature, or other aspects of the cardiovascular system of a body, e.g., a pulse rate, a blood pressure, a pulse timing, a pulse variability, a pulse transit time, an arterial stiffness, or a volume, oxygenation, flow rate, or other properties of blood in a portion of subsurface vasculature).

In such examples, the timing, duration, frequency, number, or other properties of specified periods of time during which digital codes are generated could be specified based on properties of the detected signals. In examples where the signals include light intensity signals related to the volume or other properties of blood in a portion of subsurface vasculature (i.e., photoplethysmograms) and voltage signals related to the electrical activity of the heart (i.e., electrocardiograms), the digital codes for each of the signals could be generated at a rate of more than approximately 100 Hertz. Thus, the overall rate of generation of digital codes by the ADC could be greater than a multiple of approximately 100 Hertz. For example, the multiplexer and ADC could be operated to generate digital codes based on an output of an ECG sensor, an output of a photodetector when a target of the photodetector (e.g., a portion of subsurface vasculature) is being illuminated by a first light source, the output of the photodetector when the target of the photodetector is being illuminated by a second light source, and the output of the photodetector when the target of the photodetector is being illuminated by ambient light sources. In such an example, the ADC could operate to generate digital codes at a frequency greater than approximately 400 Hertz.

To illustrate the operation of a multiplexer (e.g., 220), ADC (e.g., 240), ECG sensor (e.g., 270), photodetector (e.g., 250), light emitters (e.g., 260a, 260b), and other components (e.g., an amplifier 230) to generate such digital codes, FIG. 4 shows the relative timing of such components to generate six digital codes based on the output of a photodetector and an ECG sensor (as described elsewhere herein). The ADC timing trace 400a shows periods of time corresponding to digital codes generated by the ADC (the 'SAMPLE' level of the trace). The indicated times could correspond to periods during which a sample-and-hold is operated to transfer a value of the signal into the ADC, periods of time during which a first stage of a pipelined ADC is exposed to the signal, periods of time during which comparators or other components of an ADC are operated based on the signal, or to other aspects of the timing of operation of an ADC.

A multiplexer is configured to selectively connect the ADC (e.g., via an amplifier, filter, or some components) to outputs of the photodetector and the ECG sensor. Multiplexer timing trace 400b shows periods of time corresponding to the multiplexer connecting the output of the photodetector (the 'PD' level of the trace) or the ECG sensor (the 'ECG' level of the trace) to an amplifier, filter, or other components electrically connected to the ADC or to the ADC directly. As illustrated, the photodetector is connected to the ADC during the periods of time (as illustrated by the ADC timing trace 400a) corresponding to the first, second, fourth, and fifth digital codes generated by the ADC. The ECG sensor is connected to the ADC during the periods of time (as illustrated by the ADC timing trace 400a) corresponding to the third and sixth digital codes generated by the ADC.

The infrared timing trace (400c, 'IR') and near-infrared timing trace (400d, 'NIR') show specified periods of time corresponding to operation of first and second light emitters, respectively, to illuminate a target of the photodetector (i.e., a portion of subsurface vasculature or other region from which the photodetector is configured to receive light). Such light emitters differ in the wavelength of light they emit (e.g., the first emitting infrared light and the second emitting near-infrared light). Thus, the first and fourth generated digital codes correspond to the output of the photodetector when the photodetector's target is illuminated by the first light emitter and the second and fifth generated digital codes correspond to the output of the photodetector when the photodetector's target is illuminated by the second light emitter.

Related to the difference in wavelength of the light emitted by the light emitters, an optical property (e.g., an absorption spectrum) of the target of the photodetector (e.g., of blood in a portion of subsurface vasculature) could be determined based on a comparison between digital codes generated based on the output of the photodetector when the first light emitter is generating light and digital codes generated based on the output of the photodetector when the second light emitter is generating light. For example, an oxygenation of blood in a portion of subsurface vasculature that is the target of the photodetector could be determined based on such generated digital codes. Note that the use of infrared and near-infrared to characterize the light produced by the first and second light emitters is intended as a non-limiting example embodiment; two (or more) light emitters configured to illuminate a target of a photodetector (e.g., a portion of subsurface vasculature) could emit green lights at respective different wavelengths, lights having different polarizations and/or directions of polarization, or differing according to some other property according to an application.

Note that the configurations and operations of devices (e.g., wearable devices) as described herein are meant as non-limiting examples of devices including multiplexers configured to allow a single ADC to generate digital codes related to the outputs of two or more signal sources such that a relative timing of features of the signals output from the signal sources can be readily determined. Such signal sources could include sensors configured to detect physical variables (e.g., an intensity or other property of light, a voltage between two or more locations on or within a body) related to hemodynamic and/or physiological parameters of a human or animal body. Alternatively, such systems and methods could be applied to generate digital codes related to detected properties of a natural environment (e.g., a lake, a stream, a location in the upper atmosphere), a domestic environment (e.g., an ambient light, sound, or some other properties of a room in a house), an office environment, an industrial environment, or some other environment wherein a relative timing between two or more properties can be determined and used for an application.

III. EXAMPLE WEARABLE DEVICES

Devices and systems as described herein can be configured to be mounted to an external body surface of a wearer (i.e., can be configured as wearable devices) and to enable a variety of applications and functions including the detection of physiological and/or hemodynamic properties of the wearer (e.g., a flow rate of blood, a blood oxygenation, a blood pressure, an electrocardiographic (ECG) signal, a pulse rate, a pulse transit time), the detection of properties of the environment of the wearer (e.g., an ambient temperature, a barometric pressure), the presentation of information to the wearer (e.g., a current time, the contents of an email received by the wearer, information detected by the wearable device about physiological properties of the wearer), or other applications.

A wearable device 500 (illustrated in FIG. 5) can be configured to be mounted to and/or around a wrist or other body part or surface and to detect one or more physiological properties of the body (e.g., to detect hemodynamic properties of the body) and/or to provide other functions (e.g., to provide indications of detected hemodynamic properties, the time of day, or some other information, to communicate wirelessly with a remote system). The term "wearable device," as used in this disclosure, refers to any device that is capable of being worn at, on or in proximity to a body surface, such as a wrist, ankle, waist, chest, or other body part. In order to provide applications of the wearable device (e.g., to provide indications of information, to detect physiological parameters of a wearer), the wearable device may be positioned on a portion of the body where the wearable device can be easily viewed and/or interacted with (e.g., buttons pressed), on a portion where subsurface vasculature or other targets or elements of the body of the wearer are easily observable, or on a location according to some other consideration. The device may be placed in close proximity to the skin or tissue. Amount 510, such as a belt, wristband, ankle band, etc. can be provided to mount the device at, on or in proximity to the body surface. The mount 510 may prevent the wearable device from moving relative to the body to reduce physiological property measurement error and noise. In one example, shown in FIG. 5, the mount 510, may take the form of a strap or band 520 that can be worn around a part of the body. Further, the mount 510 may be an adhesive substrate for adhering the wearable device 500 to the body of a wearer.

A housing 530 is disposed on the mount 510 such that it can be positioned on the body. A contact surface 540 of the housing 530 is intended to be mounted facing to the external body surface. The housing 530 may include one or more sensors configured to detect one or more physiological and/or hemodynamic parameters of the wearer (e.g., a pulse rate, a blood oxygenation, a blood pressure, a blood flow rate, an electrocardiogram). Such sensors include an electrocardiogram sensor configured to detect an electrocardiogram of the wearer. The electrocardiogram sensor includes electrical contacts 555, 556 configured to electrically connect with corresponding locations of a skin surface of the wearer when the wearable device is mounted to the skin of the wearer. The electrocardiogram sensor can then detect an electrocardiogram by detecting a voltage between the electrical contacts 555, 556. Additionally or alternatively, the electrocardiogram sensor can be configured to detect and electrocardiogram by detecting a voltage between one or both of the electrical contacts 555, 556 and a third electrical contact of the device (e.g., an electrical contact that partially surrounds a display 592) that is in contact with a further skin surface of a wearer (e.g., a skin surface of a finger of an arm of the wearer that is opposite the arm to which the wearable device 500 is mounted).

The sensors further include an optical sensor 551 configured to measure a color, reflectivity, absorbance spectrum, reflectance spectrum, or some other optical properties of skin, e.g., properties that are related to a volume, an oxygenation level, a velocity, or other properties of blood in a portion of subsurface vasculature beneath the external skin surface. The optical sensor 551 includes at least one photodetector (e.g., a photodiode) configured to receive light from the external skin surface. The optical sensor 551 could additionally include one or more LEDs or other light-emitting elements configured to illuminate the external skin surface (e.g., to illuminate a portion of subsurface vasculature such that a photodetector can detect the intensity or other properties of responsively reflected, scattered, or otherwise emitted from the portion of subsurface vasculature).

The housing 530 could be configured to be water-resistant and/or water-proof. That is, the housing 530 could be configured to include sealants, adhesives, gaskets, welds, transparent windows, apertures, press-fitted seams, and/or other joints such that the housing 530 was resistant to water entering an internal volume or volumes of the housing 530 when the housing 530 is exposed to water. The housing 530 could further be water-proof, i.e., resistant to water entering an internal volume or volumes of the housing 530 when the housing 530 is submerged in water. For example, the housing 530 could be water-proof to a depth of 1 meter, i.e., configured to resist water entering an internal volume or volumes of the housing 530 when the housing 530 is submerged to a depth of 1 meter.

The wearable device 500 may also include a user interface 590 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 590 may include a display 592 where a visual indication of the alert or recommendation may be displayed. The display 592 may further be configured to provide an indication of a measured physiological parameter of a wearer.

Note that example devices herein are configured to be mounted to a wrist of a wearer. However, the embodiments described herein could be applied to other body parts (e.g., an ankle, a thigh, a chest, a forehead, a thigh, a finger). Further, embodiments described herein could be applied to devices that are not wearable, e.g., that are handheld, desktop, or otherwise configured. Further, such devices could be configured to operate in other environments than environments proximate a human body to provide other functions, e.g., to detect one or more properties of some other target environment (e.g., a natural environment, an environment of an industrial, pharmaceutical, or water treatment process).

Wearable devices and other embodiments as described herein can include a variety of components configured in a variety of ways. Devices described herein could include electronics including a variety of different components configured in a variety of ways to enable applications of the wearable device. The electronics could include controllers, amplifiers, switches, multiplexers, analog-to-digital converters, battery chargers, RF power receivers, display drivers, touch sensors, wireless communications chipsets (e.g., Bluetooth radios or other radio transceivers and associated baseband circuitry to enable wireless communications between the wearable device and some other system(s)), or other components. The electronics could include a multiplexer configured to selectively connect the output of two or more sensors of the device (e.g., the outputs of a photodetector and an electrocardiogram sensor) to and amplifier and/or ADC of the device. The controller could include a processor configured to execute computer-readable instructions (e.g., program instructions stored in data storage of the wearable device) to enable applications of the wearable device. The electronics can include additional or alternative components according to an application of the wearable device.

Wearable devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to determine some property of the wearable device and/or of the wearer of the wearable device (e.g., a hemodynamic property of a portion of subsurface vasculature and/or a health state of a wearer of the wearable device), or to provide some other functionality or application to the wearer and/or user. As one example, the wearer could press an indicated region of the user interface to indicate that the wearable device should begin logging detected medical information about the wearer. Other indicated information, changes in operation of the wearable device, or other functions and applications of the user interface are anticipated.

Note that the embodiments illustrated in the Figures are illustrative examples and not meant to be limiting. Alternative embodiments, including more or fewer components in alternative configurations are anticipated. A wearable device could include multiple housings or other such assemblies each containing some set of components to enable applications of such a wearable device. For example, a wearable device could include a first housing within which is disposed optical, electrocardiogram, or other sensors configured to detect properties of a wearer's body and a second housing containing a user interface and electronics configured to operate the sensors and to present information to and receive commands from a user of the wearable device. A wearable device could be configured to perform a variety of functions and to enable a variety of applications. Wearable devices could be configured to operate in concert with other devices or systems; for example, wearable devices could include a wireless communication interface configured to transmit data indicative of one or more detected properties of the body of a wearer of the wearable device and/or information about user inputs received from the wearer by a user interface (e.g., buttons, a touchscreen) of the wearable device. Other embodiments, operations, configurations, and applications of a wearable device as described herein are anticipated.

Figure 6:
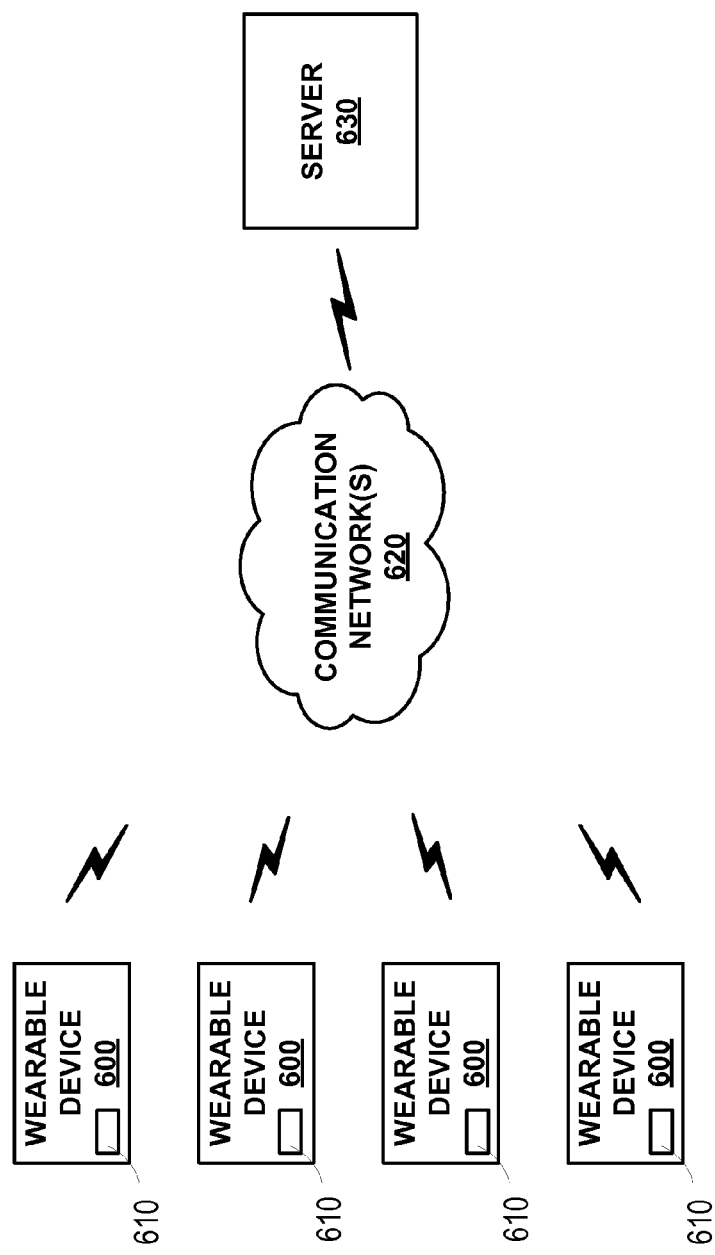
FIG. 6 is a block diagram of an example system that includes a plurality of wearable devices in communication with a server.

FIG. 6 is a simplified schematic of a system including one or more wearable devices 600. The one or more wearable devices 600 may be configured to transmit data via a communication interface 610 over one or more communication networks 620 to a remote server 630. In one embodiment, the communication interface 610 includes a wireless transceiver for sending and receiving communications to and from the server 630. In further embodiments, the communication interface 610 may include any means for the transfer of data, including both wired and wireless communications. For example, the communication interface may include a universal serial bus (USB) interface or a secure digital (SD) card interface. Communication networks 620 may be any one of may be one of: a plain old telephone service (POTS) network, a cellular network, a fiber network and a data network. In some examples, the communications interface 610 could include one or more electrical contacts of the wearable devices 600 that are configured to electrically connect to an external charger or other system(s) of the communication networks 620 such that the wearable device 600 could communicate with the communication networks 620 via the electrical contacts when the wearable devices 600 are mounted to the external charger(s). The server 630 may include any type of remote computing device or remote cloud computing network. Further, communication network 620 may include one or more intermediaries, including, for example wherein the wearable device 600 transmits data to a mobile phone or other personal computing device, which in turn transmits the data to the server 630.

In addition to receiving communications from the wearable device 600, such as collected physiological properties of a wearer or other collected information (e.g., information input by the user into the wearable devices 600 via a user interface of the devices 600), the server 630 may also be configured to gather and/or receive either from the wearable device 600 or from some other source, information regarding a wearer's overall medical history, environmental factors, user profiles, login information, geographical data, or other information. For example, a user account may be established on the server for every wearer that contains the wearer's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

Further, some embodiments of the system may include privacy controls which may be automatically implemented or controlled by the wearer of the device. For example, where a wearer's collected physiological property data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location or other information of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and hemodynamic properties, collected from his or her device may only be used for generating an individual baseline and recommendations in response to collection and comparison of his or her own data and may not be used in generating a population baseline or for use in population correlation studies.

IV. EXAMPLE DEVICE COMPONENTS

Figure 7:
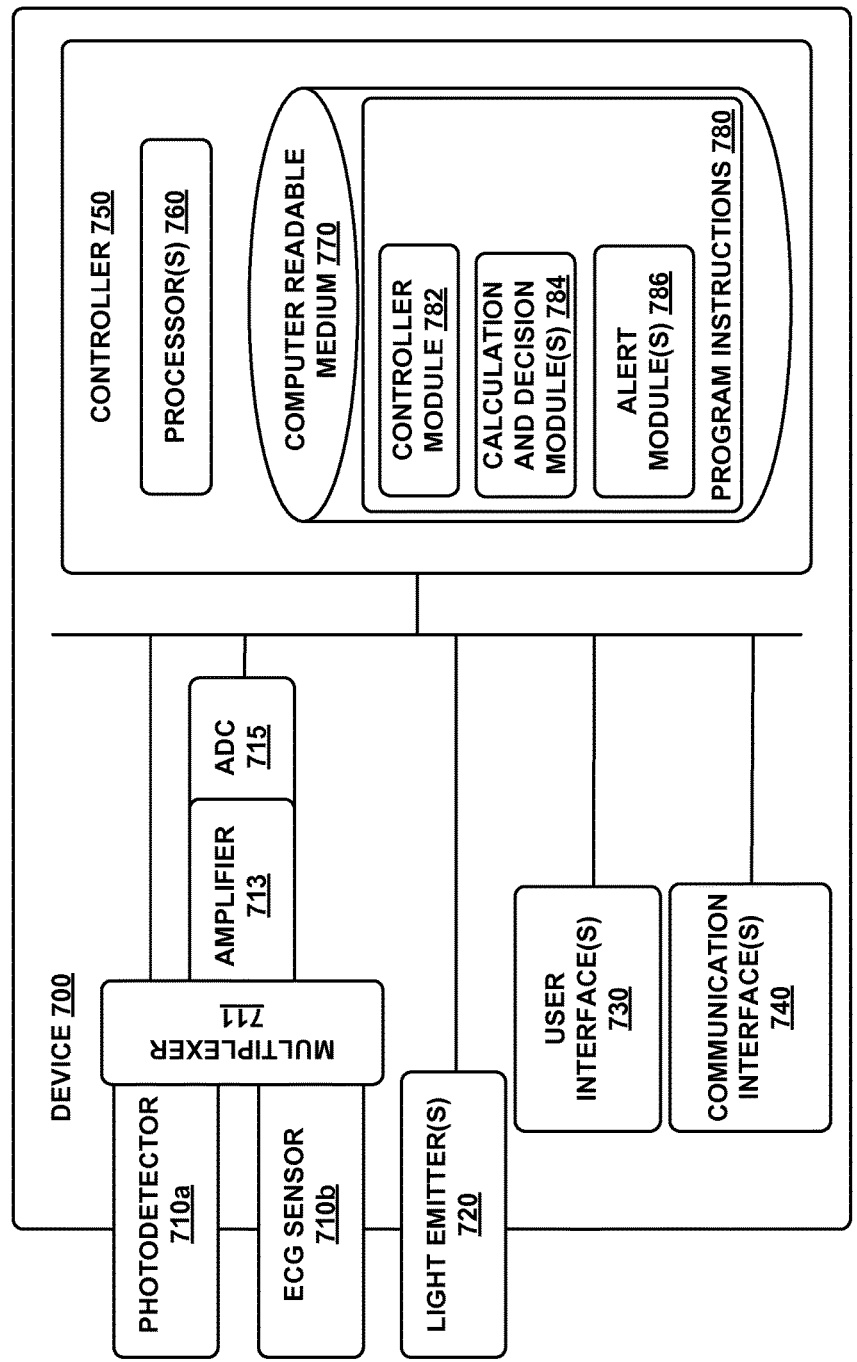
FIG. 7 is a functional block diagram of an example device.

FIG. 7 is a simplified block diagram illustrating the components of a device 700, according to an example embodiment. Device 700 may take the form of or be similar to the wearable device 500 shown in FIG. 5. However, device 700 may also take other forms, such as an ankle, waist, or chest-mounted device. Device 700 could also take the form of a device that is not configured to be mounted to a body. For example, device 700 could take the form of a handheld device configured to be maintained in proximity to an environment of interest (e.g., a body part, a biological sample container, a volume of a water treatment system) by a user or operator of the device 700 or by a frame or other supporting structure. Device 700 also could take other forms. In particular, FIG. 7 shows an example of a device 700 having a photodetector 710a, an electrocardiogram (ECG) sensor 710b, a multiplexer 711, an amplifier 713, an analog-to-digital converter (ADC) 715, and one or more light emitters 720. The device 700 further includes a user interface 730, communication interface 740 for transmitting and/or receiving data to/from a remote system, and a controller 750. The components of the device 700 may be disposed on a mount or on some other structure for mounting the device to a location of interest, e.g., to a location (e.g., a wrist) of a body of a wearer of the device 700.

Controller 750 may be provided as a computing device that includes one or more processors 760. The one or more processors 760 can be configured to execute computer-readable program instructions 780 that are stored in the computer readable data storage 770 and that are executable to provide the functionality described herein.

The computer readable medium 770 may include or take the form of one or more non-transitory, computer-readable storage media that can be read or accessed by the at least one processor 760. The one or more computer-readable storage media can include volatile and/or non-volatile storage components, such as optical, magnetic, organic or other memory or disc storage, which can be integrated in whole or in part with at least one of the one or more processors 760. In some embodiments, the computer readable medium 770 can be implemented using a single physical device (e.g., one optical, magnetic, organic or other memory or disc storage unit), while in other embodiments, the computer readable medium 770 can be implemented using two or more physical devices.

The photodetector 710a is configured to receive light from a portion of subsurface vasculature beneath a skin surface. The photodetector 710a can be configured to generate an output (e.g., an electrical current, voltage, or other signal) that is related to the intensity, wavelength, spectrum, polarization, or other properties of the received light. For example, the output of the photodetector 710a can be an electrical current related to the intensity of the received light (that is, the photodetector 710a could be a photodiode, phototransistor, or other optoelectronic element(s) configured to output a current related to the intensity of a received light), and the intensity of the received light can be related to a volume, oxygen content, hematocrit, or other properties of blood in the portion of subsurface vasculature from which the light is received. The light emitter(s) 720 are configured to illuminate the portion of subsurface vasculature with illumination having a specified wavelength, spectrum, intensity, polarization, or other properties such that at least a portion of the light received by the photodetector 710a is received from the portion of subsurface vasculature in response to illumination thereof by the light emitter(s) 720.

The light emitter(s) 720 could include one or more LEDs, lasers, or other light-emitting elements. The light emitter(s) 720 could include elements configured to emit light of a signal wavelength, e.g., a red, green, or near-infrared wavelength that is specified to be transmitted through the skin and/or other intervening tissues and to be absorbed by, scattered by, or to otherwise interact with blood (e.g., with hemoglobin or other chromophores in the blood) in the portion of subsurface vasculature. Thus, the intensity or other properties of the light responsively emitted from the portion of subsurface vasculature and received by the photodetector 710a can be related to one or more properties (e.g., a relative or absolute volume, a flow rate, a hematocrit, an oxygen content or saturation) of blood in the portion of subsurface vasculature. In some examples, the light emitter(s) 720 could be configured to emit light at different wavelengths and/or otherwise having different spectral contents during respective different time periods (e.g., during respective different pluralities of time periods, e.g., respective different pluralities of sampling times) such that a blood oxygenation or other properties of the blood can be determined based on the intensity or other properties of the light received by the photodetector 710a in response to illumination of the portion of subsurface vasculature by light of respective different wavelengths.

Figure 5:
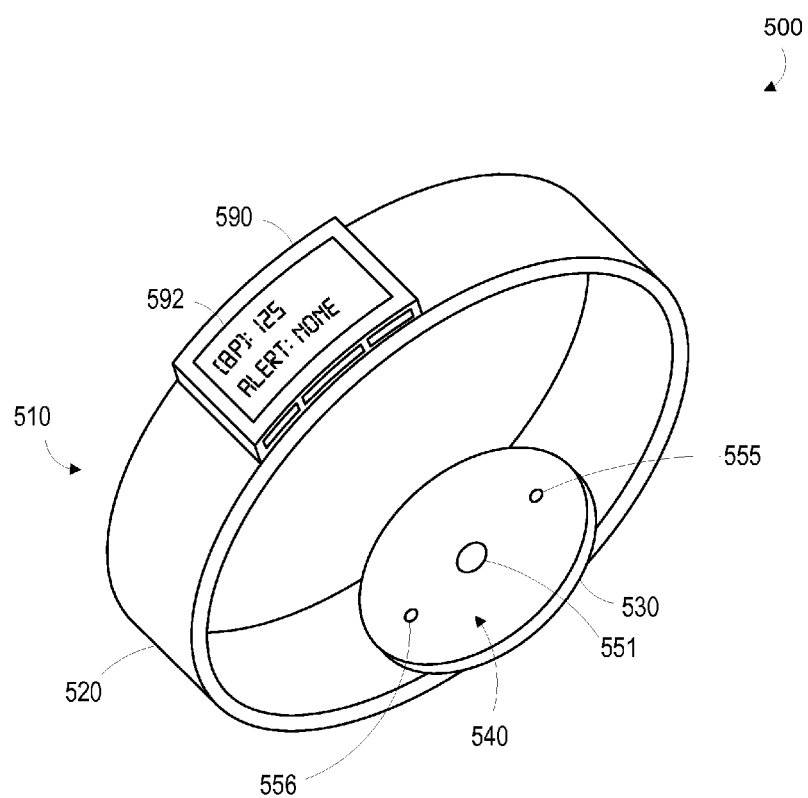
FIG. 5 is a perspective view of an example wearable device.

The ECG sensor 710b is configured to generate an output (e.g., an output voltage and/or current) related to an electrocardiogram detected between two or more points on skin surfaces of a user. This could include detecting a voltage between two or more electrical contacts that are mounted to respective different locations of the skin surface of the user. Such different locations could be different locations on a single arm of the user (e.g., locations on a wrist of a user to which the electrical contacts 555, 556 of the example wearable device 500 of FIG. 5 are mounted). Additionally or alternatively, such different locations could be locations on first and second arms of the wearer (e.g., a wrist location of a first arm to which one of the electrical contacts 555, 556 is mounted an a finger or other skin location of an opposite arm that has been brought into contact with a further electrical contact of the example wearable device 500), locations on the chest of a user, or some other skin locations of a human body. The electrical contacts could be configured to electrically connect and/or couple to skin surfaces capacitively, ohmically, or in some other manner.

The ECG sensor 710b could include amplifiers, instrumentation amplifiers, automatic gain controls, filters, buffers, or other electronic components configured to detect an ECG using two or more electrical contacts and to generate an output having a voltage, current, or other properties related to the detected ECG. Such an output could be related to the detected ECG by a gain, an offset, a nonlinear relationship, or some other relationship. The ECG sensor 710b could be configured to provide some other functionality, e.g., to detect an impedance between two or more electrical contacts, to detect whether two or more electrical contacts are mounted to skin of a user (e.g., by detecting an impedance and/or capacitance between the electrical contacts), to disable the output of the ECG sensor 710b (e.g., when the electrical contacts are not mounted to skin, when the multiplexer 711 is not electrically connecting the output of the ECG sensor 710b to the amplifier 713 and ADC 715), or according to some other application.

In some examples, the device 700 could include three (or more) electrical that are connected to the ECG sensor 710b and that are configured to be mounted to the skin of a person at respective different skin locations. The ECG sensor 710b could be configured detect an electrocardiogram signal from voltage fluctuations between first and second electrical contacts. The ECG sensor 710b could be further configured to drive a third electrical contact according to an average of the signals present at the first and second electrical contacts, e.g., to reduce a common-mode signal present at the first and second electrical contacts. That is, the ECG sensor 710b could use the third electrical contact to reduce a voltage difference between the device 700 (e.g., a ground of the device, the first and second electrical contacts of the device) and the body of the person.

The multiplexer 711 is configured to selectively connect an output of the photodetector 710a, an output of the ECG sensor 710b, and/or one or more further outputs of further sensors or other components to an input of the amplifier 713. This could include operating one or more electronic switches (e.g., bipolar transistors, field-effect transistors) to, during respective different periods of time, connect the different outputs (e.g., of 710a and 710b) to the input of the amplifier. Such switching could include connecting a single electrical signal from the output of one of the signal sources (e.g., 710a, 710b) to the amplifier 713 (i.e., the outputs could be single-ended signals). Additionally or alternatively, such switching could include connecting two or more electrical signals from the output of one of the signal sources (e.g., 710a, 710b) to the amplifier 713 (e.g., the outputs could be differential signals). Such switching could additionally include connecting the output(s) of non-selected signal sources (e.g., the photodetector 710a, the ECG sensor 710b, some other sensor(s)) to a specified impedance or other signal sink or other component(s).

The amplifier 713 could include a variety of different components (e.g., transistors, operational amplifiers, active or passive filters, level shifters, buffers) configured to provide an output electrical signal to the ADC 715 that is related to a signal received from the photodetector 710a, ECG sensor 710b, or some other signal source via the multiplexer 711. This could include applying a gain, an offset, or some other relationship between a property of a received signal (e.g., the magnitude of a current received by the amplifier 713 via the multiplexer 711) and a generated signal (e.g., the magnitude of a voltage) that is applied to an input of the ADC 715. For example, the amplifier 713 could be configured to apply a gain and offset to a received input signal such that a generated signal applied to the ADC 715 has values within a dynamic range of the ADC 715. In some examples, the amplifier 713 could be a transimpedance amplifier that is configured to apply a specified reverse bias voltage to the photodetector 710a (e.g., to a photodiode of the photodetector 710a) and to generate an output signal related to the magnitude of current through the photodetector 710a when the multiplexer 711 is operated to connect the amplifier 713 and the photodetector 710a.

The ADC 715 is configured to generate digital codes (e.g., digital codes representing binary digital values) related to electrical signals received from the amplifier 713. The generated digital codes could represent binary values, delta modulated bit streams, or could have other relationships to the voltage, current, or other properties of signals received from the amplifier 713 at and/or during one or more points and/or periods of time. The ADC 715 could include one or more comparators, oscillators, sample-and-holds, integrators, digital switches, differentiators, amplifiers, operational amplifiers, digital-to-analog converters, sigma-delta modulators, or other components configured as a flash ADC, an integrating ADC, a successive-approximation ADC, a pipelined ADC, a sigma-delta ADC, or in some other way to generate a plurality of digital codes based on an electrical signal received via the multiplexer 711 during respective sampling times or sampling periods. The ADC 715 could be configured to produce digital codes having a specified resolution, e.g., digital codes having a resolution of 22 bits.

The program instructions 780 stored on the computer readable medium 770 may include instructions to perform any of the methods described herein. For instance, in the illustrated embodiment, program instructions 780 include a controller module 782, a calculation and decision module 784, and an alert module 786.

Controller module 782 may include instructions for operating the multiplexer 711, ADC 715, light emitter(s) 720, and/or other components (e.g., the ECG sensor 710b) to generate data (e.g., digital codes) related to one or more physiological and/or hemodynamic properties of a body. This could include operating the multiplexer 711 to selectively connect the photodetector 710a, ECG sensor 710b, and/or other sensors to the amplifier 713 during respective pluralities of specified periods of time (e.g., respective pluralities of sampling times or sampling periods) and operating the ADC 715 to generate respective pluralities of digital codes based on the output of the amplifier 713 during such specified periods of time. This could further include operating the light emitter(s) 720 to illuminate a portion of subsurface vasculature during one or more of the pluralities of specified periods of time.

In some examples, the amplifier 713, ADC 715, one or more drivers configured to operate the light emitter(s) 720, or other components of the device 700 could be provided as a single integrated circuit. Such an integrated circuit could include a digital oscillator, finite state machine, or other components configured to control a timing of the digital codes generated by the ADC 715, the timing of operation of the multiplexer 711, the timing of illumination generated by the light emitter(s) 720, or other operations of the device 700 to detect optical and/or electrical signals using the photodetector 710a, ECG sensor 710b, and/or other sensors. In such examples, the controller module 782 could include instructions for operating such components and/or integrated circuits, e.g., for setting a timing and/or rate of sampling of the ADC 715, for setting a number of bits or other properties of the digital codes generated by the ADC 715 (e.g., setting the ADC 715 generate digital codes with an effective resolution of 22 bits), for setting a relative timing and/or identity of signals selected by the multiplexer 711, or to set some other properties of operation of the ADC 715, amplifier 713, multiplexer 711, light emitter(s) 720, or some other components. Further, the controller module 782 could include instructions for beginning the operation of such components, e.g., for sending a start command to such components, for providing a clock signal to such components, for receiving and/or accessing digital codes generated by the ADC 715, or for performing some other operations related to generating and/or receiving digital codes related to optical and/or electrical signals using the ADC 715.

The calculation and decision module 784 may include instructions for using digital codes generated by the ADC 715 to determine one or more hemodynamic or other physiological properties of a user. Such determinations could include detecting peaks, maxima, minima, or other features of an optical, electrical or other signal detected using the photodetector 710a, ECG sensor 710b, or other sensors. Such determinations could further include determining a pulse rate, pulse timing, pulse variability, or other hemodynamic properties of a user by, e.g., determining properties of one or more peaks or other features of detected optical, electrical, or other signals. In some examples, the calculation and decision module 784 could include instructions to compare the timing of features (e.g., peaks, heartbeats) of signals detected using the photodetector 710a (e.g., photoplethysmographic signals related to the volume and/or flow of blood in a portion of subsurface vasculature) and the timing of features of signals detected using the ECG sensor 710b (e.g., QRS complexes of a detected electrocardiogram). For example, a time difference between peaks of a detected electrocardiogram and a detected photoplethysmographic signal could be used to determine a pulse transit time. For example, a time difference between the activity of the heart to pump blood during a particular heartbeat (as detected electrically, using the ECG sensor) and a corresponding change in volume and/or flow of blood in a portion of subsurface vasculature (as detected optically, using the photodetector 710a) could be determined. Such a determined pulse transit time could be used to determine a stiffness of the portion of subsurface vasculature, a blood pressure, or some other physiological, hemodynamic, or health information about a user.

The controller module 782 can further include instructions for operating a user interface 720. For example, controller module 782 may include instructions for displaying data collected using the ADC 715 and analyzed by the calculation and decision module 784, or for displaying one or more alerts generated by the alert module 786. The controller module 782 can include instructions for operating the user interface 730 based on a determination of the calculation and decision module 784 (e.g., a determined pulse rate, blood pressure, pulse transit time, arterial stiffness, blood oxygenation, or other hemodynamic and/or physiological parameters). Controller module 782 may include instructions for displaying data related to a user account of a user, e.g., a number of unread emails in a user's email account, the content of an email received by the user, or some other information. Further, controller module 782 may include instructions to execute certain functions based on inputs accepted by the user interface 720, such as inputs accepted by one or more buttons disposed on the user interface.

Communication interface(s) 740 may also be operated by instructions within the controller module 782, such as instructions for sending and/or receiving information via a wireless antenna, which may be disposed on or in the device 700. The communication interface 740 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

The computer readable medium 770 may further contain other data or information, such as medical and health history of a user of the device 700, user account information, user credentials (e.g., usernames, passwords, cryptographic keys and/or certificates), that may be useful in performing functions of the device 700. In some examples, the device 700 could be configured to detect one or more physiological and/or hemodynamic parameters of a user (e.g., a heart rate, a blood oxygenation, a blood pressure, the presence and/or concentration of one or more analytes in the blood of a wearer) and the computer readable medium 770 could contain information related to such physiological parameter detection (e.g., sensor calibration information, physiological parameter baselines of a user, physiological parameter levels indicative of a medical condition). The calculation and decision module 784 may be configured to use such stored information to determine whether a wearer is experiencing a medical condition and may further, upon determining that such a medical or other emergency condition is indicated, generate one or more recommendations for the user of the device 700 based, at least in part, on consultation of a clinical protocol. Such recommendations may alternatively be generated by a remote server and transmitted to the device 700.

In some examples, information collected by the device 700 (e.g., collected physiological parameter data, baseline profiles, health state information input by device users) may be input to a cloud network and be made available for download by a user's physician. Trend and other analyses may also be performed on the collected data, such as hemodynamic property data and health state information, in the cloud computing network and be made available for download by physicians or clinicians.

In response to a determination by the calculation and decision module 784 that a medical or other specified condition is indicated, the alert module 786 may generate an alert via the user interface 720. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication. Additionally or alternatively, the alert module 786 may generate an alert via the communication interface(s) 740 such that the alert is communicated to a remote system, e.g., a server in a physician's office, emergency room, or other locations in a hospital, a server in an emergency medical services and/or police department dispatch office, or some other remote systems.

V. EXAMPLE METHODS

Figure 8:
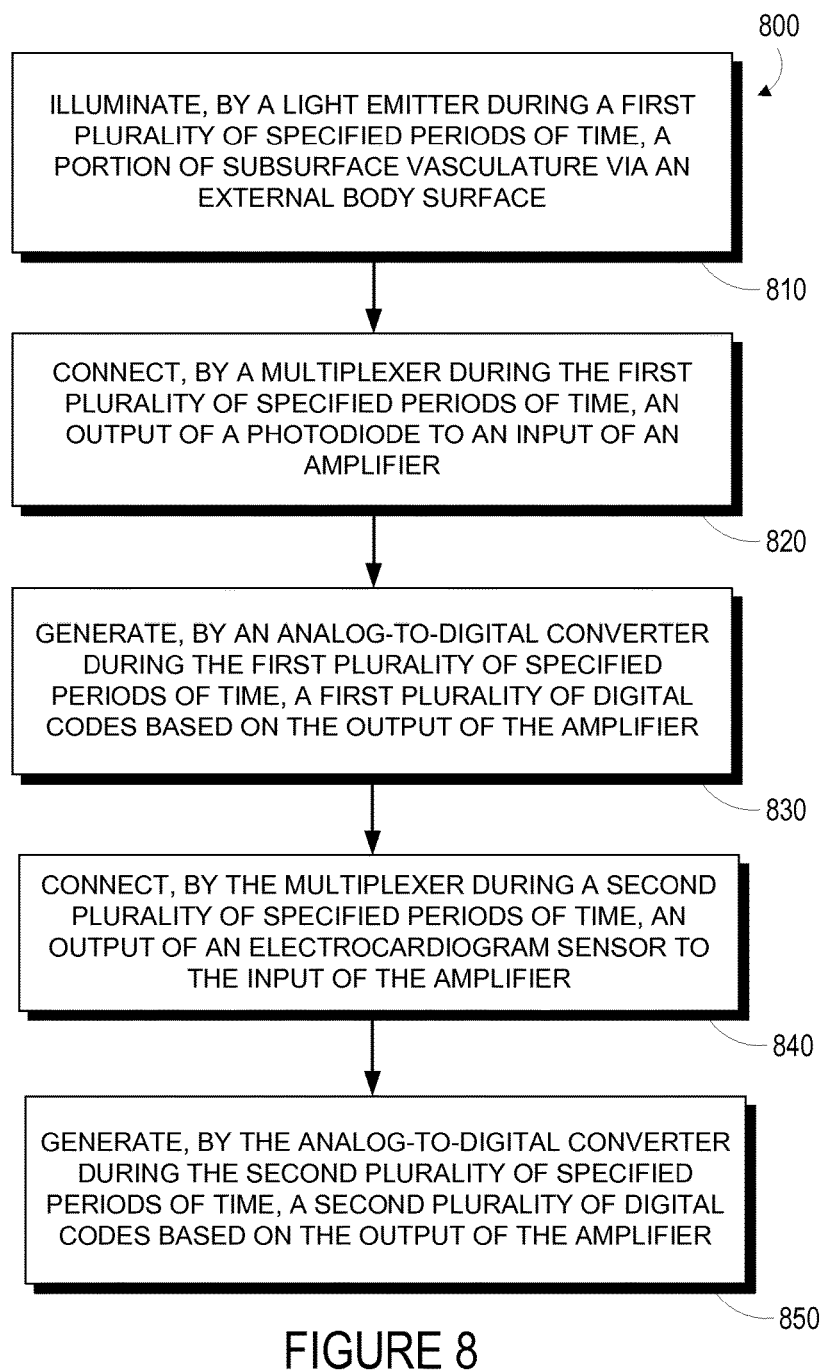
FIG. 8 is a flowchart of an example method.

FIG. 8 is a flowchart of a method 800. The method 800 includes illuminating, by a light emitter operated by a controller during a first plurality of specified periods of time, a portion of subsurface vasculature via an external body surface (810). This could include illuminating the portion of subsurface vasculature with light having a specified wavelength, spectral content, degree and/or direction of polarization, coherence length, or having some other specified properties. The external body surface could be any location on the skin of a body where subsurface vasculature is easily visible, e.g., a wrist of a person. The plurality of specified periods of time could have substantially the same duration and could have a regular timing, e.g., could comprise a specified duration of time (e.g., approximately 2.5 milliseconds) repeated at a specified frequency (e.g., approximately 100 Hertz).

The method 800 also includes connecting, by a multiplexer operated by the controller during the first plurality of specified periods of time, an output of a photodetector to an input of an amplifier (820). The photodetector is configured to receive light emitted from the portion of subsurface vasculature responsive to illumination by the light emitter. The photodetector could include a photodiode, phototransistor, or other optoelectronic element(s) that can be reverse-biased (e.g., by an amplifier that is configured as a transimpedance amplifier) and configured such that a current through the photodetector (e.g., through a photodiode of the photodetector) is proportional to the intensity of the light received by the photodetector form the portion of subsurface vasculature. The photodetector could include a filter, grating, or other optical elements configured to substantially block light outside of one or more ranges of wavelengths from being received by the photodetector, to control a direction from which the photodetector receives light, or to otherwise modify and/or control light received by the photodetector from the portion of subsurface vasculature.

The method 800 also includes generating, by an analog-to-digital converter (ADC) operated by the controller during the first plurality of specified periods of time, a first plurality of digital codes based on the output of the amplifier (830). This could include generating a plurality of digital codes representing binary values related to the signal output by the photodetector during the first plurality of specified periods of time. Generating a particular digital code could include operating a sample-and-hold circuit to transfer the magnitude of a signal received form the amplifier to one or more other components of the ADC during a corresponding particular specified time period of the plurality of specified time periods. Generating a particular digital code could include generating a delta-modulated bit stream based on the magnitude of the signal received from the amplifier during the corresponding particular specified time period and determining a digital code having a specified number of bits (e.g., more than approximately 22 bits) based on a number of bits of the delta-modulated bit stream. Generating a particular digital code could include clocking a pipelined ADC during the corresponding specified time period and during one or more subsequent time periods.

The method 800 also includes connecting, by the multiplexer operated by the controller during a second plurality of specified periods of time, an output of an electrocardiogram sensor to the input of the amplifier (840). The electrocardiogram sensor is configured to detect an electrocardiographic signal via the external body surface. The ECG sensor could include amplifiers, buffers, level shifters, filters, or other components configured to detect a time-varying voltage between two points of the external body surface (e.g., via two electrical contacts or electrodes) that is related to the electrical activity of the heart. This could include detecting a voltage between two points on the chest, arm(s), wrist, leg(s), or other parts of a body. For example, the ECG sensor could detect an electrocardiogram based on a voltage between two points on a wrist of a person. Additionally or alternatively, the ECG sensor could detect an electrocardiogram based on a voltage between a first electrical contact mounted to a wrist of a person and a second electrical contact that the person is touching with a finger or other element of an arm opposite the arm to which the first electrical contact is mounted.

The method 800 for operating a wearable device could include additional steps relating to detection of optical and electrical signals via an external skin surface, generating pluralities of digital codes based on such detected signals, and using such generated digital codes to determine information (e.g., physiological and/or hemodynamic parameters) about a human body. For example, the controller, photodetector, electrocardiogram sensor, light emitter, multiplexer, amplifier, and ADC could be part of a wearable device and the method 800 could include mounting the wearable device to the external body surface using a mount. The method 800 could include operating the multiplexer and ADC to generate additional pluralities of digital codes based on the outputs of additional sensors during corresponding pluralities of specified periods of time. Additionally or alternatively, the method 800 could include operating the multiplexer and ADC to generate additional pluralities of digital codes based on the output of the photodetector (or some other sensor or signal source) during corresponding pluralities of specified periods of time, e.g., when the portion of subsurface vasculature is being illuminated by a further light emitter (e.g., a light emitter that emits illumination of a different wavelength, spectral content, or other properties than the light emitter used to illuminate the portion of subsurface vasculature during the first plurality of specified periods of time).

The method 800 could include determining a hemodynamic or other parameter of the body based on multiple pluralities of generated digital codes corresponding to respective different detected signals. For example, the method 800 could include determining a pulse transit time, an arterial stiffness, a blood pressure, or some other hemodynamic parameters based on the first and second pluralities of digital codes. This could include determining a time difference between the timing of a feature in a detected electrocardiogram (e.g., by detecting the feature in the second plurality of digital codes) and the timing of a corresponding feature in a detected photoplethysmogram (e.g., by detecting the feature in the first plurality of digital codes). The method 800 could include determining other hemodynamic and/or physiological parameters or other information based on digital codes generated by the ADC and/or other information sources. The method 800 could include determining health states of a person based on such determined hemodynamic and/or physiological parameters. For example, the method 800 could include determining whether a person is experiencing tachycardia, arrhythmia, bradycardia, hypovolemia, anemia, sleep apnea, atherosclerosis, hypertension, hypotension, orthostatic hypotension, or some other health state based on a detected pulse rate, pulse timing, pulse variability, blood oxygenation, blood pressure, arterial stiffness, blood flow rate, or some other determined parameter of the person.

The method 800 could further include providing indications related to such determinations, e.g., providing an indication on a display of a wearable device that includes the light emitter, photodetector, ECG sensor, multiplexer, amplifier, and ADC, providing a wireless indication to a remote system (e.g., a server, a cellphone), or providing an indication in some other way. Such indications could include indications of values of determined parameters (e.g., the value of a determined heart rate, blood pressure, blood oxygenation), indications of determined health states (e.g., an event of arrhythmic heart activity), indications of activities that a person should undertake related to a determined health state or physiological parameter (e.g., to take a medication, to seek emergency medical assistance), or some other indications.

The example method 800 illustrated in FIG. 8 is meant as an illustrative, non-limiting example. Additional or alternative elements of the method and additional or alternative components of a wearable or otherwise-configured device are anticipated, as will be obvious to one skilled in the art.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a light emitter, wherein the light emitter is configured to illuminate a portion of subsurface vasculature via an external body surface;
   a photodetector, wherein the photodetector is configured to receive light emitted from the portion of subsurface vasculature responsive to illumination by the light emitter;
   an electrocardiogram sensor, wherein the electrocardiogram sensor is configured to detect an electrocardiographic signal via the external body surface;
   an amplifier;
   a multiplexer, wherein the multiplexer is electrically connected to an output of the photodetector, an output of the electrocardiogram sensor, and an input of the amplifier, and wherein the multiplexer is controllable to selectively connect the output of the photodetector and the output of the electrocardiogram sensor to the input of the amplifier;
   an analog-to-digital converter, wherein the analog-to-digital converter is configured to generate digital codes based on an output of the amplifier; and
   a controller, wherein the controller is configured to perform controller operations comprising:
      operating the light emitter, during a first plurality of specified periods of time, to illuminate the portion of subsurface vasculature;
      operating the multiplexer, during the first plurality of specified periods of time, to connect the output of the photodetector to the input of the amplifier;
      operating the analog-to-digital converter to generate a first plurality of digital codes based on the output of the amplifier during the first plurality of specified periods of time;
      operating the multiplexer, during a second plurality of specified periods of time, to connect the output of the electrocardiogram sensor to the input of the amplifier, wherein the second plurality of specified periods of time are offset in time from the first plurality of specified periods of time; and
      operating the analog-to-digital converter to generate a second plurality of digital codes based on the output of the amplifier during the second plurality of specified periods of time.

2. The system of claim 1, wherein the external body surface is a wrist location.

3. The system of claim 1, further comprising:
   a display, wherein the controller operations further include operating the display to provide an indication based on at least one digital code generated by the analog-to-digital converter.

4. The system of claim 1, wherein the analog-to-digital converter is a sigma-delta analog-to-digital converter.

5. The system of claim 1, wherein the amplifier is a transimpedance amplifier and the photodetector is a photodiode.

6. The system of claim 1, further comprising at least one electrical contact connected to the electrocardiogram sensor and a mount configured to mount the light emitter, photodetector, and at least one electrical contact proximate to the external body surface.

7. The system of claim 1, further comprising:
   a further light emitter, wherein the further light emitter is configured to illuminate the portion of subsurface vasculature via the external body surface, wherein the photodetector is configured to receive light emitted from the portion of subsurface vasculature responsive to illumination by the further light emitter, and wherein the controller operations further comprise:
      operating the further light emitter, during a third plurality of specified periods of time, to illuminate the portion of subsurface vasculature;
      operating the multiplexer, during the third plurality of specified periods of time, to connect the output of the photodetector to the input of the amplifier;
      operating the analog-to-digital converter to generate a third plurality of digital codes based on the output of the amplifier during the third plurality of specified periods of time.

8. The system of claim 7, wherein the controller operations further comprise determining a blood oxygenation based on the first plurality of digital codes and the third plurality of digital codes.

9. The system of claim 1, wherein the controller operations further comprise determining a pulse transit time based on the first plurality of digital codes and the second plurality of digital codes.

10. The system of claim 1, wherein the amplifier and the analog-to-digital converter are provided on a single integrated circuit.

11. The system of claim 1, further comprising:
    a transmitter, wherein the controller operations further include operating the transmitter to provide a wireless indication based on at least one digital code generated by the analog-to-digital converter.

12. The system of claim 1, wherein the controller operations further comprise determining a pulse rate based on the first plurality of digital codes or the second plurality of digital codes.

13. The system of claim 1, wherein the controller operations further comprise determining a blood pressure based on at least one of the first plurality of digital codes or the second plurality of digital codes.

14. A method comprising:
illuminating, by a light emitter operated by a controller during a first plurality of specified periods of time, a portion of subsurface vasculature via an external body surface;
connecting, by a multiplexer operated by the controller during the first plurality of specified periods of time, an output of a photodetector to an input of an amplifier, wherein the photodetector is configured to receive light emitted from the portion of subsurface vasculature responsive to illumination by the light emitter;
generating, by an analog-to-digital converter operated by the controller during the first plurality of specified periods of time, a first plurality of digital codes based on the output of the amplifier;
connecting, by the multiplexer operated by the controller during a second plurality of specified periods of time, an output of an electrocardiogram sensor to the input of the amplifier, wherein the second plurality of specified periods of time are offset in time from the first plurality of specified periods of time, and wherein the electrocardiogram sensor is configured to detect an electrocardiographic signal via the external body surface; and
generating, by the analog-to-digital converter operated by the controller during the second plurality of specified periods of time, a second plurality of digital codes based on the output of the amplifier.

15. The method of claim 14, further comprising:
providing an indication based on at least one digital code generated by the analog-to-digital converter.

16. The method of claim 14, further comprising:
illuminating, by a further light emitter operated by the controller during a third plurality of specified periods of time, the portion of subsurface vasculature via the external body surface;
connecting, by the multiplexer operated by the controller during the third plurality of specified periods of time, the output of the photodetector to the input of the amplifier, wherein the photodetector is configured to receive light emitted from the portion of subsurface vasculature responsive to illumination by the further light emitter; and
generating, by the analog-to-digital converter operated by the controller during the third plurality of specified periods of time, a third plurality of digital codes based on the output of the amplifier.

17. The method of claim 14, further comprising:
determining a pulse transit time based on the first plurality of digital codes and the second plurality of digital codes.

18. The method of claim 14, further comprising:
providing a wireless indication based on at least one digital code generated by the analog-to-digital converter.

19. The method of claim 14, further comprising:
determining a pulse rate based on the first plurality of digital codes or the second plurality of digital codes.

20. The method of claim 14, further comprising:
determining a blood pressure based on the first plurality of digital codes or the second plurality of digital codes.

* * * * *